(12) United States Patent
Conrad et al.

(10) Patent No.: US 9,165,189 B2
(45) Date of Patent: Oct. 20, 2015

(54) SEED HOLDING DEVICE AND SEED CLASSIFICATION SYSTEM WITH SEED HOLDING DEVICE

(71) Applicant: BALL HORTICULTURAL COMPANY, West Chicago, IL (US)

(72) Inventors: Robert Scott Conrad, Wheaton, IL (US); Xiaolei Hu, Aurora, IL (US)

(73) Assignee: BALL HORTICULTURAL COMPANY, West Chicago, IL (US)

( * ) Notice: Subject to any disclaimer, the term of this patent is extended or adjusted under 35 U.S.C. 154(b) by 50 days.

(21) Appl. No.: 13/941,094

(22) Filed: Jul. 12, 2013

(65) Prior Publication Data

US 2013/0294656 A1    Nov. 7, 2013

Related U.S. Application Data

(63) Continuation-in-part of application No. 13/186,004, filed on Jul. 19, 2011, now Pat. No. 8,605,149.

(51) Int. Cl.
*G06K 9/00* (2006.01)
*A01C 1/00* (2006.01)
*G01N 21/25* (2006.01)
(Continued)

(52) U.S. Cl.
CPC .............. *G06K 9/00536* (2013.01); *A01C 1/00* (2013.01); *G01N 21/253* (2013.01); *G01N 21/6486* (2013.01); *G06K 9/00* (2013.01); *G01N 21/6452* (2013.01); *G02B 21/0004* (2013.01); *G06K 2209/17* (2013.01)

(58) Field of Classification Search
CPC ...... G01B 11/022; G01B 11/024; H04N 7/18; H04N 7/181; G01C 15/00
See application file for complete search history.

(56) References Cited

U.S. PATENT DOCUMENTS

| 5,253,302 A | 10/1993 | Massen |
| 5,841,883 A | 11/1998 | Kono et al. |
| 5,864,984 A | 2/1999 | McNertney |

(Continued)

FOREIGN PATENT DOCUMENTS

| DE | 29815605 U1 | 12/1998 |
| DE | 19845883 A1 | 5/1999 |

(Continued)

OTHER PUBLICATIONS

Draper, S.R. et al., "Machine Vision for the Characterization and Identification of Cultivars," Plant Varieties and Seeds 2:53-62 (1989).

(Continued)

*Primary Examiner* — Dave Czekaj
*Assistant Examiner* — Nam Pham
(74) *Attorney, Agent, or Firm* — Marshall, Gerstein & Borun LLP

(57) ABSTRACT

A seed classification system is provided. The seed classification system includes a seed holding device and a seed spectral analysis system. The seed holding device includes a top surface and a plurality of wells disposed in the top surface. The plurality of wells are configured to hold a plurality of seeds. Each well is defined by at least one wall extending transverse to the top surface. The seed spectral analysis system is configured to obtain image data for one or more of the seeds held in one or more of the wells of the seed holding device and configured to classify the one or more seeds based on the obtained image data.

10 Claims, 27 Drawing Sheets

(51) Int. Cl.
  *G02B 21/00* (2006.01)
  *G01N 21/64* (2006.01)

(56) References Cited

U.S. PATENT DOCUMENTS

| | | |
|---|---|---|
| 6,080,950 A | 6/2000 | Jalink |
| 6,114,683 A | 9/2000 | Spiering et al. |
| 6,366,681 B1 | 4/2002 | Hutchins |
| 6,563,122 B1 | 5/2003 | Ludeker et al. |
| 6,567,537 B1 | 5/2003 | Anderson |
| 6,646,264 B1 | 11/2003 | Modiano et al. |
| 6,882,740 B1 | 4/2005 | McDonald, Jr. et al. |
| 7,112,806 B2 | 9/2006 | Lussier |
| 7,123,750 B2 | 10/2006 | Lu et al. |
| 7,142,988 B1 | 11/2006 | Johnson |
| 7,199,376 B2 | 4/2007 | Prange et al. |
| 7,218,775 B2 | 5/2007 | Kokko et al. |
| 7,289,646 B2 | 10/2007 | Hirahara et al. |
| 7,367,155 B2 | 5/2008 | Kotyk et al. |
| 7,499,573 B2 | 3/2009 | Tanabata et al. |
| 7,617,057 B2 | 11/2009 | May et al. |
| 8,375,628 B2 | 2/2013 | Petersen et al. |
| 2003/0021469 A1 | 1/2003 | Kato et al. |
| 2005/0074146 A1 | 4/2005 | Jones et al. |
| 2008/0031067 A1 | 2/2008 | Lovett |
| 2008/0304710 A1 | 12/2008 | Xu et al. |
| 2008/0310674 A1* | 12/2008 | Modiano et al. ............ 382/100 |
| 2009/0161102 A1 | 6/2009 | Deppermann et al. |
| 2009/0260281 A1 | 10/2009 | Conrad |
| 2010/0042234 A1 | 2/2010 | May et al. |
| 2010/0111369 A1 | 5/2010 | Lussier |
| 2011/0307974 A1* | 12/2011 | Beemster et al. ............ 800/285 |

FOREIGN PATENT DOCUMENTS

| | | |
|---|---|---|
| DE | 102008039456 A1 | 3/2009 |
| EP | 1154370 A2 | 11/2001 |

OTHER PUBLICATIONS

Draper, S.R. et al., "Preliminary Observations with a Computer Based System for Analysis of the Shape of Seeds and Vegetative Structures," J. Nata. Inst. Agric. Bot. 36:387-395 (1984).
International Search Report for Application No. PCT/US2012/047056 dated Oct. 5, 2012.
Keefe, P.D. et al., "An Automated Machine Vision System for the Morphometry of New Cultivars and Plant Genebank Accessions," Plant Varieties and Seeds 1:1-11 (1988).
Keys, R.D. et al., "Automated Seedling Length Measurement for Germination/Vigor Estimation Using a CASAS (Computerized Automated Seed Analysis System)," J. of Seed Technol. 9:40-53 (1984).
McCormac, A.C. et al., "Automated Vigor Testing of Field Vegetables Using Image Analysis," Seed Sci. & Technol. 18:103-112 (1990).
McCormac, A.C. et al., "Cauliflower (*Brassica oleracea* L.) Seed Vigour: Imbibition Effects," J. of Exp. Bot. 41:893-899 (1990).
Travis, A.J. et al., "A Computer Based System for the Recognition of Seed Shape," Seed Sci. & Technol. 13:813-820 (1985).
Written Opinion for Application No. PCT/US2012/047056 dated Oct. 5, 2012.

* cited by examiner

[Pansy:Well:24-OnLid]
count = "8"
step1 = "ExtractPlane:red,buffer1;"
step2 = "ExtractPlane:green,buffer2;"
step3 = "Operation:buffer1,add,buffer2,buffer3;"
step4 = "Threshold:250,255,buffer3,buffer3;"
step5 = "BinaryReverse:buffer3,buffer3;"
step6 = "Remove_Border:buffer3,buffer3;"
step7 = "Keep_Largest:100,buffer3,Well Mask;"
step8 = "FillHole:Well Mask,Well Mask;"

[Pansy:Whole Plant:24-OnLid]
count = "16"
step1 = "ExtractPlane:hue,buffer1;"
step2 = "ExtractPlane:saturation,buffer2;"
step3 = "Operation:buffer1,add,buffer2,buffer2;"
step4 = "Threshold:250,255,buffer2,buffer2;"
step5 = "BinaryReverse:buffer2,buffer2;"
step6 = "Mask:Well Mask,buffer2,Plant Parts;"
step7 = "ExtractPlane:red,buffer1;"
step8 = "ExtractPlane:green,buffer2;"
step9 = "Operation:buffer1,muldiv,buffer2,buffer2;"
step10 = "Threshold:240,255,buffer2,buffer2;"
step11 = "Mask:Well Mask,buffer2,buffer3;"
step12 = "Operation:buffer3,or,Plant Parts,Plant Parts;"
step13 = "Width_Shrink:6,Plant Parts,Plant Parts;"
step14 = "Keep_Largest:50,Plant Parts,Plant Parts;"
step15 = "FillHole:Plant Parts,Plant Parts;"
step16 = "Width_Filter:30,Plant Parts,Plant Parts;"

[Pansy:Leaf:24-OnLid]
count = "5"
step1 = "Operation:chlor_high,clearif<,35.00,buffer1;"
step2 = "Threshold:5,255,buffer1,buffer1;"
step3 = "FillHole:buffer1,leaf;"
step4 = "Mask:Well Mask,leaf,leaf;"
step5 = "Shift:-70,-80,leaf,leaf;"

*FIG. 13A*

[Pansy:Stem:24-OnLid]
count = "7"
step1 = "Operation:chlor_high,clearif<=,5.00,buffer2;"
step2 = "Threshold:5,255,buffer2,buffer2;"
step3 = "FillHole:buffer2,stem;"
step4 = "Mask:Well Mask,stem,stem;"
step5 = "Shift:-70,-80,stem,stem;"
step6 = "BinaryReverse:leaf,buffer1;"
step7 = "Mask:buffer1,stem,stem;"

[Pansy:Root:24-OnLid]
count = "10"
step1 = "ExtractPlane:blue,buffer1;"
step2 = "ExtractPlane:saturation,buffer2;"
step3 = "Operation:buffer1,add,buffer2,buffer3;"
step4 = "Threshold:1,200,buffer3,buffer3;"
step5 = "FillHole:buffer3,buffer3;"
step6 = "Keep_Largest:100,buffer3,buffer3;"
step7 = "Width_Filter:10,buffer3,buffer1;"
step8 = "Mask:buffer1,buffer3,buffer3;"
step9 = "BinaryReverse:buffer3,root;"
step10 = "Mask:root,Plant Parts,root;"

*FIG. 13B*

[Pansy:Seed:24-OnLid]
count = "8"
step1 = "Operation:leaf,or,stem,buffer1;"
step2 = "Operation:buffer1,or,root,buffer2;"
step3 = "BinaryReverse:buffer2,seed;"
step4 = "Mask:seed,Plant Parts,seed;"
step5 = "Width_Shrink:10,seed,seed;"
step6 = "ConvexHull:seed,buffer1;"
step7 = "BinaryReverse:buffer1,buffer1;"
step8 = "Mask:buffer1,root,root;"

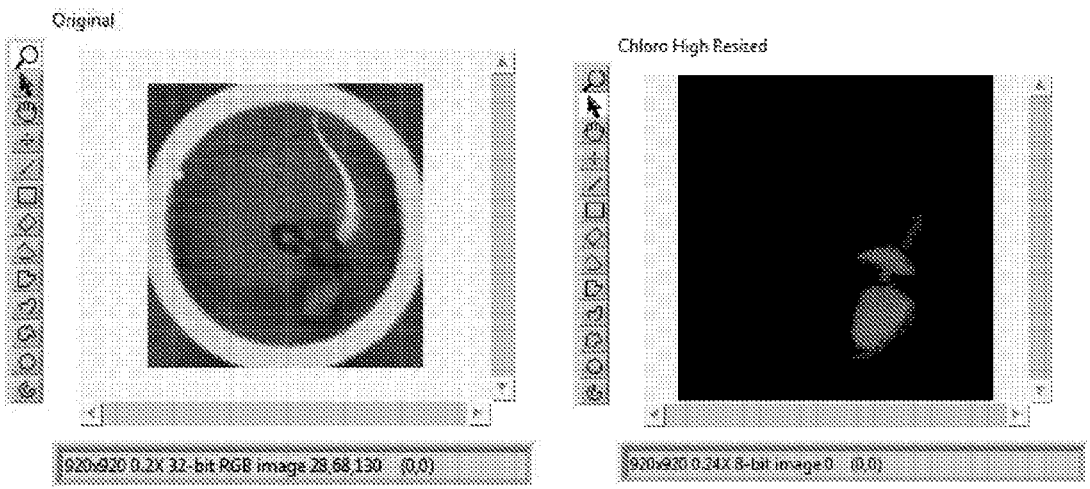
FIG. 18A
FIG. 18C
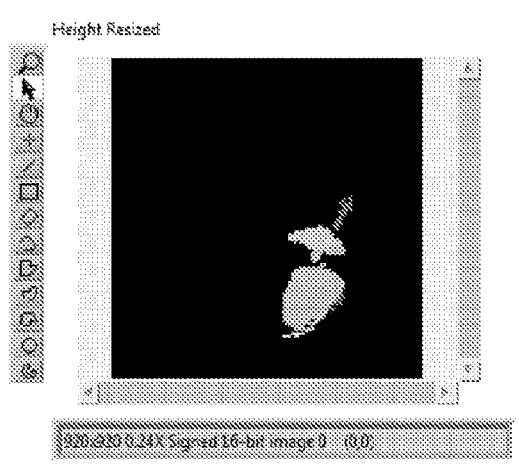
FIG. 18B
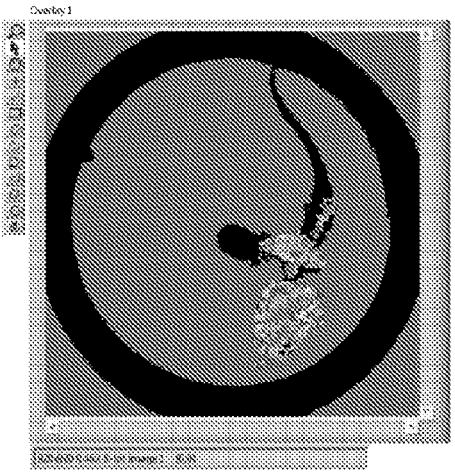
FIG. 18D

SEED HOLDING DEVICE AND SEED CLASSIFICATION SYSTEM WITH SEED HOLDING DEVICE

RELATED APPLICATION DATA

This application is a continuation-in-part of U.S. patent application Ser. No. 13/186,004, filed Jul. 19, 2011, which is hereby incorporated by reference herein in its entirety.

FIELD OF TECHNOLOGY

This disclosure relates to a method and system that models a seed structure and uses spectral analysis to identify which morphological structures are existent in the seed/seedling. Additionally, this disclosure relates to a method and system that applies multi-spectral analysis using predetermined models of a seed/seedling to identify which morphological structures are existent in the seed/seedling. The information about the existence or non-existence of structures of the seed/seedling is used to classify the seed as having a specific characteristic, for later commercial use or sale. The seed market determines which specific characteristic the method will use to classify the seed/seedling.

DESCRIPTION OF THE BACKGROUND ART

The background art of seed analysis that uses spectrum analysis is directed to image analysis of roots or leaves.

Background art that uses image analysis to analyze seed roots uses an image scanner to obtain an image of a plurality of seedlings that are pressed into blotter paper. Software is used to process the seedlings image to remove the background from the image and thus isolate the plurality of seedlings. Then the software uses thresholding techniques to analyze the image of the seedlings to produce a resulting binary image of seedlings.

Because not all of the seedlings are usually neatly aligned, the seedlings may cross over each other. The software identifies which seedlings are physically crossing each other in the seedling image. The seedlings image information is further processed by software to determine the medial axis for each seedling, which is referred to as a "skeleton" of each seeding. All of the identifiable objects in the binary seedlings image are labeled with three things: a unique object label, the two-dimensional x-y axis bounds of that object, and the total number of pixels in that object. The software then determines the separation point between each seedling's hypocotyl and radicle using a stochastic minimization method. The software then determines the length of the hypocotyl and radicle of the root, and then generates a seed vigor rating of the seedlings based on these measurements, and weighted user defined factors.

The background art method is relatively calculation intense, does not classify structures of a plant besides a hypocotyl and a radicle, which are both parts of a root, and is not applicable to different types of seed/seedlings.

SUMMARY OF THE DISCLOSURE

One aspect of the present disclosure includes a seed holding device for use with a seed spectral analysis system. The seed holding device includes a top layer that defines a plurality of openings and a bottom layer coupled to the top layer. The seed holding device further includes a plurality of wells formed by the openings in the top layer and an upper surface of the bottom layer. The plurality of wells are configured to hold a plurality of seeds.

Another aspect of the present disclosure includes a method for providing a customized seed holding device for a seed classification system. The method includes determining maximum exterior dimensions of the seed holding device, and obtaining a first layer of the material for the seed holding device based on the determined maximum exterior dimensions. The method also includes identifying one or more seeds to be classified. The method further includes forming one or more openings for the one or more seeds in an interior of the first layer of material based on the identified one or more seeds to be classified.

DESCRIPTION OF THE DRAWINGS

FIGS. 13 (13A-13B) illustrates an example classification script for the seed structures that are classified as shown in FIG. 17C-17D.

FIG. 18A-18G illustrate images that may be produced with the seed analysis system and methods described herein, and then used to determine seed classification, and thus seed lot germination.

DETAILED DESCRIPTION

Terminology

Figure 1:
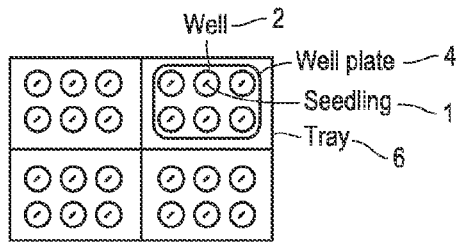
FIG. 1 is a diagram of an example tray of well plates that may hold one or more seeds/seedlings for analysis.

For ease of reading, this disclosure uses the term "seed" to indicate a seed, which has been subjected to imbibition so that it may develop further, that is, a seed manifesting imbibition-induced development, which is how one of ordinary skill in the art may phrase such a seed. Accordingly, the term "seed" herein refers to a seed in any stage of development including, or in between, the stages including: the stage of the seed before germination, upon germination, on through to the final stage of a developed plant.

For example, the terms "growth-induced seed," "seed manifesting imbibition-induced development," "imbibed seed," "germinated seed," "seed," "seed going through the germination process," "seedling," "small plant," and "plant" are used interchangeably throughout this document, and as such are intended to have the meaning which includes all of the stages included by these terms including in-between and end stages, as these terms are used broadly and are intended to include a seed as it goes through all the stages of the growth process on to its development into a plant.

The definitions of the morphological structures of a seed are not currently universally agreed upon in the industry and art. This disclosure encompasses a seed classification system, devices, and method for using spectral analysis to determine the existence of seed structures in all types of seeds as they mature, including all corresponding seed structures. Thus, to encompass the scope of the structures that develop from a seed until the seed has matured beyond a practical size for analysis, the disclosure herein presents examples of the morphological structures and example groupings to provide a better understanding of the seed classification concepts discussed herein.

Example Seed Structures

The method and system for using spectral analysis to determine the existence of seed structures described herein may be useful in establishing an estimated percent of germination for a group of seeds. A seed typically contains an embryonic plant. Seed germination is the resumption of normal growth from a dormant embryonic plant that is inside a seed. For example, a seed of a flowering plant or gymnosperm contains an embryo and stored food reserves inside a seed coat. Plants produce varying numbers of seeds of which some may lack embryos and thus never germinate. In another case, a seed may have an embryo, but if the seed is not allowed to germinate within some certain length of time, then the embryo inside may die. Different seeds have a different length of viability, which may vary from a few weeks up to 2000 years. A mature seed may be placed in favorable conditions. If the seed fails to germinate, it is said to be dormant. The time a seed remains dormant may be reduced or eliminated by the applications of seed treatments. Seed treatments that may be used to induce germination include, for example, stratification, vernalization, and soaking. In the commercial sale of seeds it is useful to have an estimate of what percentage of a seed lot will germinate.

Germination implies complex physical and chemical changes. These changes develop as the seed embryo develops a young shoot and a root. The first root of a germinated seed is a radicle. The first stem of a germinated seed is a cotyledon. A typical young seedling includes a root system (i.e. root) including the radicle (embryonic root) and the shoot system (i.e., stem) including the hypocotyl (embryonic shoot) and the cotyledons (seed leaves). New roots grow from root meristems located at the tip of the root, and new stems and leaves grow from shoot meristems located at the tip of the shoot.

The seed structures, such as seed coat, hilium, micropyle, testa, along with others that are known in the field (but not listed here for purposes of keeping the disclosure practical) may be defined as being a part or a sub-structure of a seed structure.

The seed structures, such as embryonic root, radicle, root tip, root meristem, along with others that are known in the field (but not listed here for purposes of keeping the disclosure practical) may be defined as being a part or sub-structure of a root structure.

The seed structures, such as embryonic shoot, shoot meristem, epicotyl, plummule, coleoptiles, shoot, stem, hypocotyls, hook, round cotyledon, along with others that are known in the field (but not listed here for purposes of keeping the disclosure practical) may be defined as being a part or sub-structure of a shoot or, as termed herein, stem structure.

The developmental stage usually considered the final stage of interest in germination testing is the evaluation of primary or "true" leaf development. The first "true" leaves expand and can often be distinguished from the round cotyledons through their species-dependent distinct shapes.

The seed structures: "true leaf," cotyledon leaf, along with others that are known in the field (but not listed here for purposes of keeping the disclosure practical) may be defined as being a part or sub-structure of a leaf structure.

Seed germination may be further explained using two different seed types, such as a dicotyledon seed type and a monocotyledon seed type. A dicotyledon type of seed is a seed which typically has two embryonic leaves or cotyledons (a.k.a seed-leafs.) Whereas, a monocotyledon is a seed which typically has one cotyledon.

FIGS. 10A-10G illustrate a dicotyledon type of seed that is germinated in a lab environment. FIGS. 10A-10G include examples of seed structures that may be identified with the method and system described herein. The example seed structures of FIGS. 10A-10G are of a pansy seed. Other species' seeds may be analyzed with the embodiments described herein.

Figure 10A:
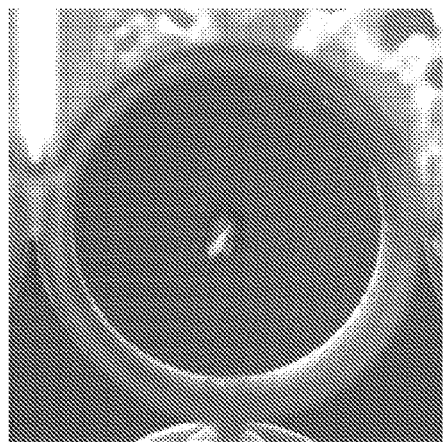
FIGS. 10A-10G illustrate example structures of an example seed for analysis.
Figure 10C:
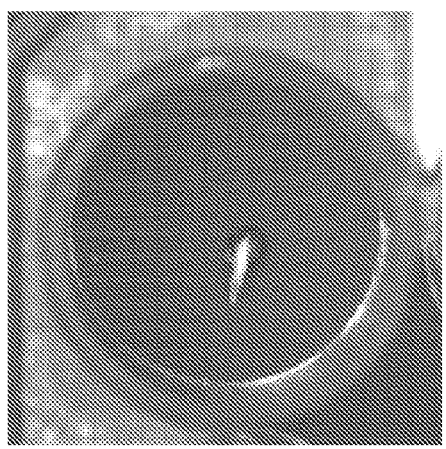
Figure 10B:
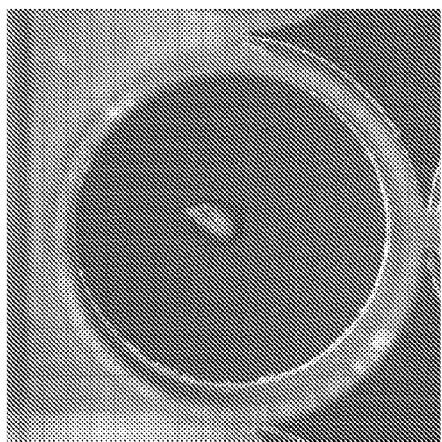

FIG. 10A illustrates a pansy seed after it has been imbibed with water. The seed splits and root growth begins. The root begins to grow and cotyledons grow to expand and then break the surrounding seed coat. The root tip emerges as illustrated in FIG. 10B. As the root structure continues to elongate, as illustrated in FIG. 10C, chlorophyll has not yet developed. The root is defined to be the structure seen emerging from the seed, usually a white colored structure that does not have detectable chlorophyll.

Figure 10D:
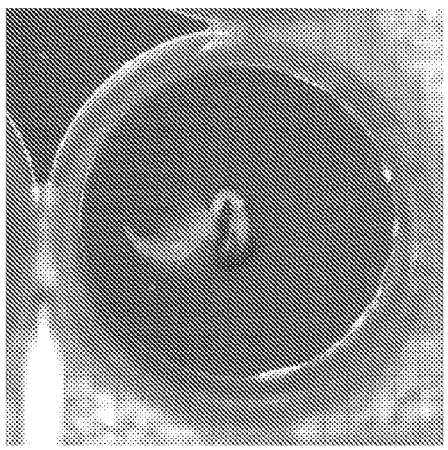
Figure 10E:
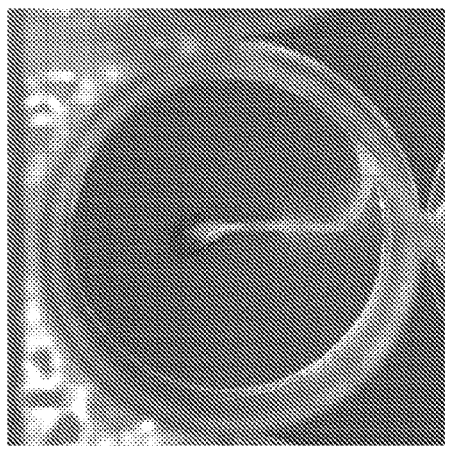
Figure 10G:
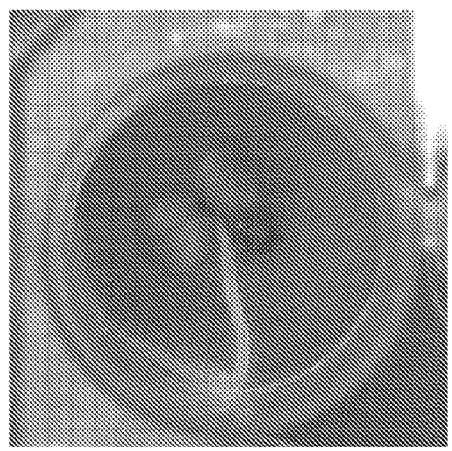
Figure 10F:
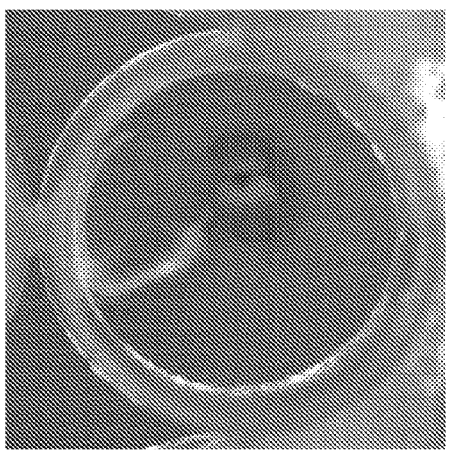

FIG. 10D illustrates the start of a hypocotyl developing. The hypocotyl starts to expand and form a hook structure. At this stage chlorophyll starts to develop to where it may be detectable. FIG. 10E illustrates a hypocotyl that continues to grow to where it becomes straight, and the hook has disappeared. At this stage chlorophyll continues to accumulate. FIG. 10F illustrates the seed as having grown cotyledons extending out of the seed coat. The cotyledons may be partially opened. FIG. 10G illustrates the seed having reached a stage of development where the cotyledons have grown out of the seed coat and are open and fully expanded. At this stage the chlorophyll continues to accumulate.

As stated above, the disclosure herein presents examples of morphological structures of a seed to provide a better understanding of the types of seed structures that may be classified using the method and system described herein. The seed structure classification results may be used to determine seed germination values that are used in commercial sale of the seed and its associated seed lot.

Figure 19:
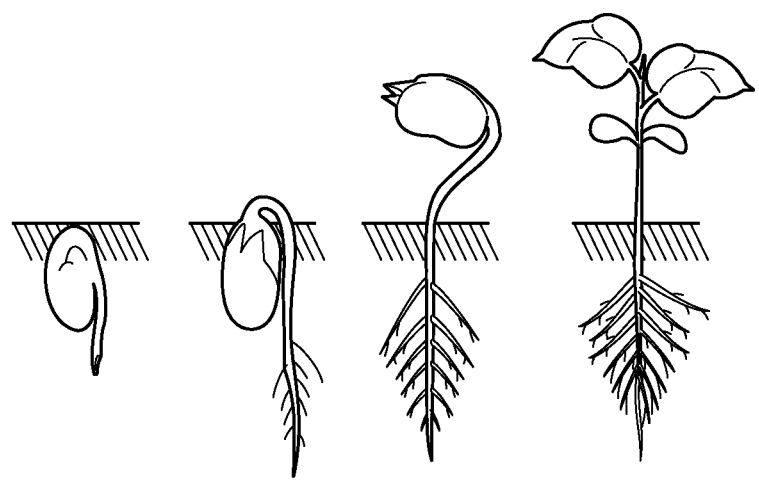
FIG. 19 illustrates an example of the structures of a dicotyledon type seed during germination.
Figure 20:
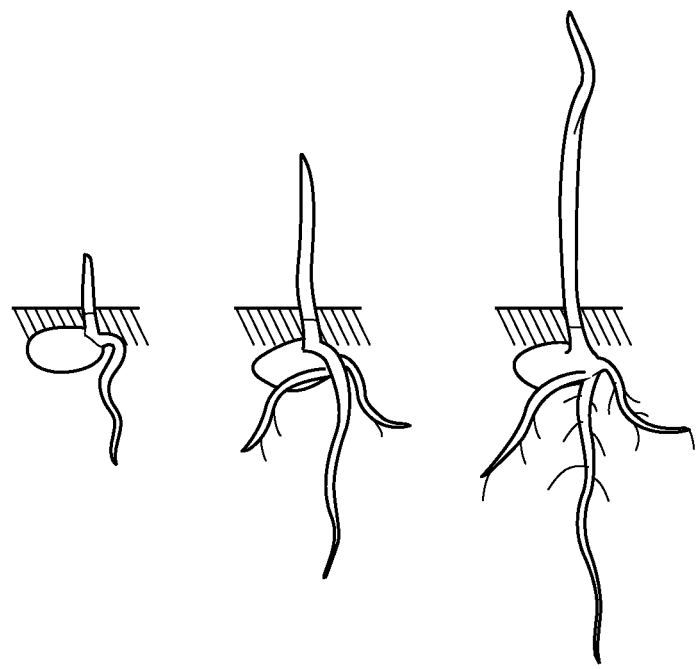
FIG. 20 illustrates an example of the structures of a monocotyledon type seed during germination.

Another example of the seed structures as they develop during germination are illustrated in FIGS. 19 and 20. In particular, FIG. 19 and FIG. 20 illustrate examples of how seeds that were placed in soil may develop. FIGS. 19 and 20 illustrate the example development of two different types of seeds. FIG. 19 illustrates the scenario when a dicotyledon type of seed is germinated. FIG. 20 illustrates the scenario when a monocotyledon type of seed is germinated.

FIG. 19 illustrates the structures that may be produced from a dicotyledon type of seed as it grows in soil. First a primary root emerges from the seed coat. Then a hypocotyl emerges from the seed coat, and is formed in between the root and the seed coat. The hypocotyl may push the seed coat up above the soil. The two cotyledons (seed-leafs) protect the seed's epicotyls structures, such as the plummule, from mechanical damage that may occur while moving through the soil. After the hypocotyl emerges from the soil, it straightens out. Then the cotyledons may spread apart and expose the epicotyl. The epicotyl has the primary leaf s and the apical meristem. In many dicotyledons the cotyledons support the plant by providing a food reserve for the developing plant. The cotyledons may also support the plant by turning green and using photosynthesis to produce more food for the plant before they drop off.

FIG. 20 illustrates the structures that may be produced from a monocotyledon type of seed as it grows. A primary root pierces the seed and grows down into the soil. The primary leaf of the monocotyledon plant grows up. The primary leaf of the monocotyledon plant is protected by a hollow cylindrical structure, which is termed a coleoptile. After the seedling has grown above the soil surface, the coleoptiles stops growing and the seedling's primary leaf emerges and expands out.

Plant development is the process by which seed structures originate and mature as a plant grows. These developmental processes can be collectively referred to as stages of germination and may be characterized according to the respective morphological features that form. These features are termed as "seed structures" herein. The general terms of seed coat, root, stem (i.e. shoot), and leaf are termed as "seed structures" herein, while all other structures, including the other structures described herein and used in the art, are termed as "sub-structures" which may fall under the more general "seed structure" categories, or similar categories for use in classification of the seed.

Example Embodiments

FIG. 1 illustrates an example embodiment. A seed 1 may be placed in an individual seed well 2. There may be six wells to a well plate 4. A tray 6 may hold four well plates. A single tray of well plates may contain twenty-four individual seeds that are located in respective wells. The tray 6 of seeds may be automatically placed, such as by a robotic well plate handling device (see robotic handler 10 in FIG. 2) in a seed analysis scanner device, for example scanner device 20 (FIG. 2).

The well plate 4 may contain a different numbers of wells 2, for example ninety-six wells, or any other number within practical limitation. The individual well 2 may be of a size that would produce an image of, for example, 1,000 by 1,000 pixels. The well 2 is used to isolate a single seed 1 for imaging and analysis purposes.

The well 2 may contain a seed 1 that was imbibed with water alone, for example on a filter paper, paper towel, or paper blotter, etc. Alternatively, the well 2 may contain the imbibed seed 1 in soil or other growing media. The seed 1 may be sowed into the soil. A "plug test" is a term that is used to indicate that the seed 1 was sown into soil. Whereas, the term "lab test" denotes that the seed 1 was imbibed with water, but was not placed in soil. However, the seeds 1 may be incubated in any way. The seed 1 is placed in a well 2 so that the analysis of the seed 1 may be more easily automated by the seed analysis system 200 of FIG. 2.

Figure 2:
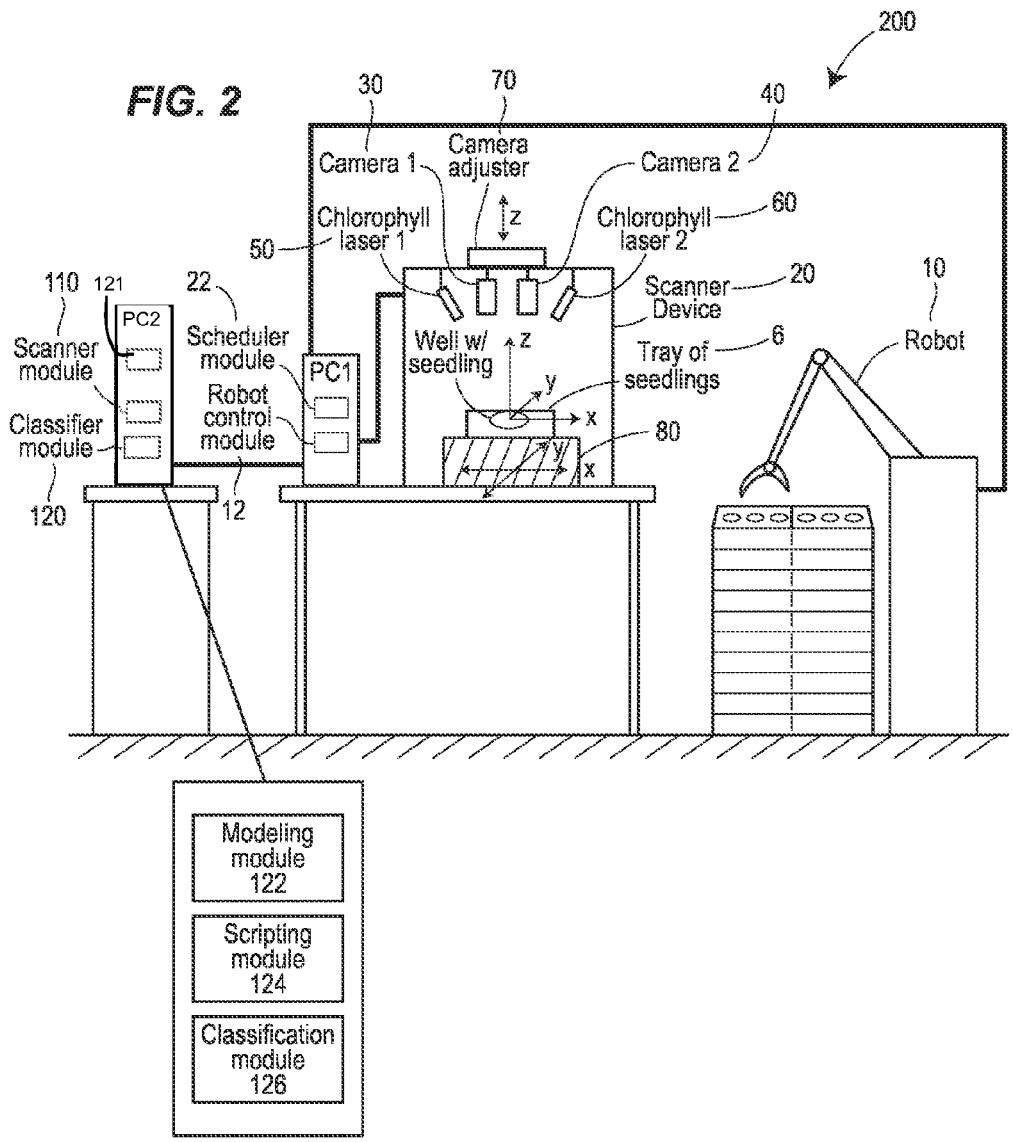
FIG. 2 is a diagram of an example seed/seedling analysis system.

The well plates 4 may be stacked or configured in a way so that a robotic handler 10 may easily move a well plate 4, and thus a given individual seed 1, to a location that is suitable for analysis of the seed 1 by, for example, the scanner device 20 of FIG. 2.

Figure 11A:
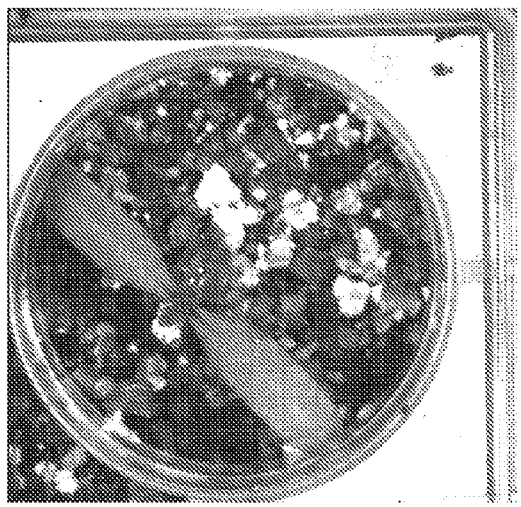
FIGS. 11A-11C illustrate an example of multi-spectral image inputs for use in classification processing.

Alternatively, the tray 6 may include well plates 4 of wells 2 that are each filled with soil and a seed 1. The well plate 4 may have sides that are high enough to encompass and isolate the individual seed 1 as it grows. The image illustrated in FIG. 11A is top view of an example of a seed growth resulting from seed 1 being placed in this type of well plate 4 and soil tray configuration.

For example, a seed holding device that would have sides closures that are high enough to encompass and isolate the individual seed 1 as it grows include a well plate 4 that is covered with one or more well plates 4, wherein the well plates that may be stacked that have their respective bottom surfaces removed so that such well plates 4 may be stacked on top of the bottom well plate 4 that is actually holding the seeds 1. In this way, the seed 1 may be kept to its individual well surrounding and not cross over to any adjacent well. Keeping the seed 1 within a prescribed well 2 location helps to assure that the applied spectral analysis of the seed is of only the single seed 1.

FIG. 2 illustrates an example embodiment of a seed spectral analysis system 200 disclosed herein. An example seed analysis system 200 includes a well plate robot handling device 10, a scanner device 20, a movable platform stage 80 (on which the well plates are located during analysis), a first recording device e.g., camera 30, a second recording device e.g., camera 40, a first laser source 50 (e.g., first chlorophyll laser), a second laser source 60 (e.g., second chlorophyll laser), a camera adjuster 70, a robot control module 12, a scheduler module 22, a scanner module 110, and a classifier module 120. In some embodiments, the seed analysis system 200 includes a customization module 121.

The scanner device 20 may include the hardware and/or software devices that may be used to capture seed data, for example: platform stage 80, a first recording device e.g., camera 30, a second recording device e.g., camera 40, a first laser source 50, a second laser source 60, and a camera adjuster 70.

The controlling software modules may be stored inside the housing of a specialized computing device that is configured to control the seed analysis system 200. For example, the robot control module 12, scheduler module 22, scanner module 110, customization module 121, and classifier module 120 may be stored inside the housing of two separate specialized computers so that a user may have better visibility and control over the controlling software modules, as illustrated in FIG. 2.

Other alternative storage and execution configurations may be used in accordance with embodiments disclosed herein. For example, all of the robot control module 12, scheduler module 22, scanner module 110, customization module 121, and classifier module 120 may be stored in memory at a single computing device, or they may be stored in memory at distributed computing devices throughout the system 200, or anything in between, and executed similarly.

The robot device 10 includes robotics hardware/software/assemblies and controls that are used to move the single well plate tray 6, with seeds 1 to be analyzed, from a stack of trays to the platform stage 80. The robot assembly may also include a conveyor belt (not shown) for initially moving the next needed well plate from a well plate storage location (not shown) to within reach of the robot device 10. An x-y-z coordinate system may be used by the robot 10 to reference the placement of the tray 6. For example, an x-y axis may form a plane that is parallel to the top surface of the platform stage 80. The scanner module 110 may be used to control the x-y location of the seed via movement of the platform stage 22 in relation to, for example, a first camera 30. The overhead camera adjuster 70 may be used to control the distance in a z direction from the seed in the well plate tray 6 to the first camera 30.

The first camera 30 may be a charge coupled device (CCD) camera, or any other camera type of imaging or image recording device that is capable of sensing and/or recording visible spectrum information from the seed. The first camera 30 may be used to obtain a first visible spectrum two-dimensional image of an individual seed. The overhead camera adjuster 20 may adjustably move the first camera 30 vertically to a position in the z direction from the seed so that the image captured by the first camera would produce a well-defined 1000 by 1000 pixel image of the individual seed. The first camera 30 may be configured to automatically focus on the selected single seed within the selected single well. Alternatively, the first camera 30 may capture images of multiple seeds at a time, which may later be processed by the scanner module 110 to divide the group image into respective images of individual seeds. The customization module 121 is configured to customize the seed holding device, such as the tray 6 or the seed holding device 2000, as will be described below.

Example Methods

Figure 3:
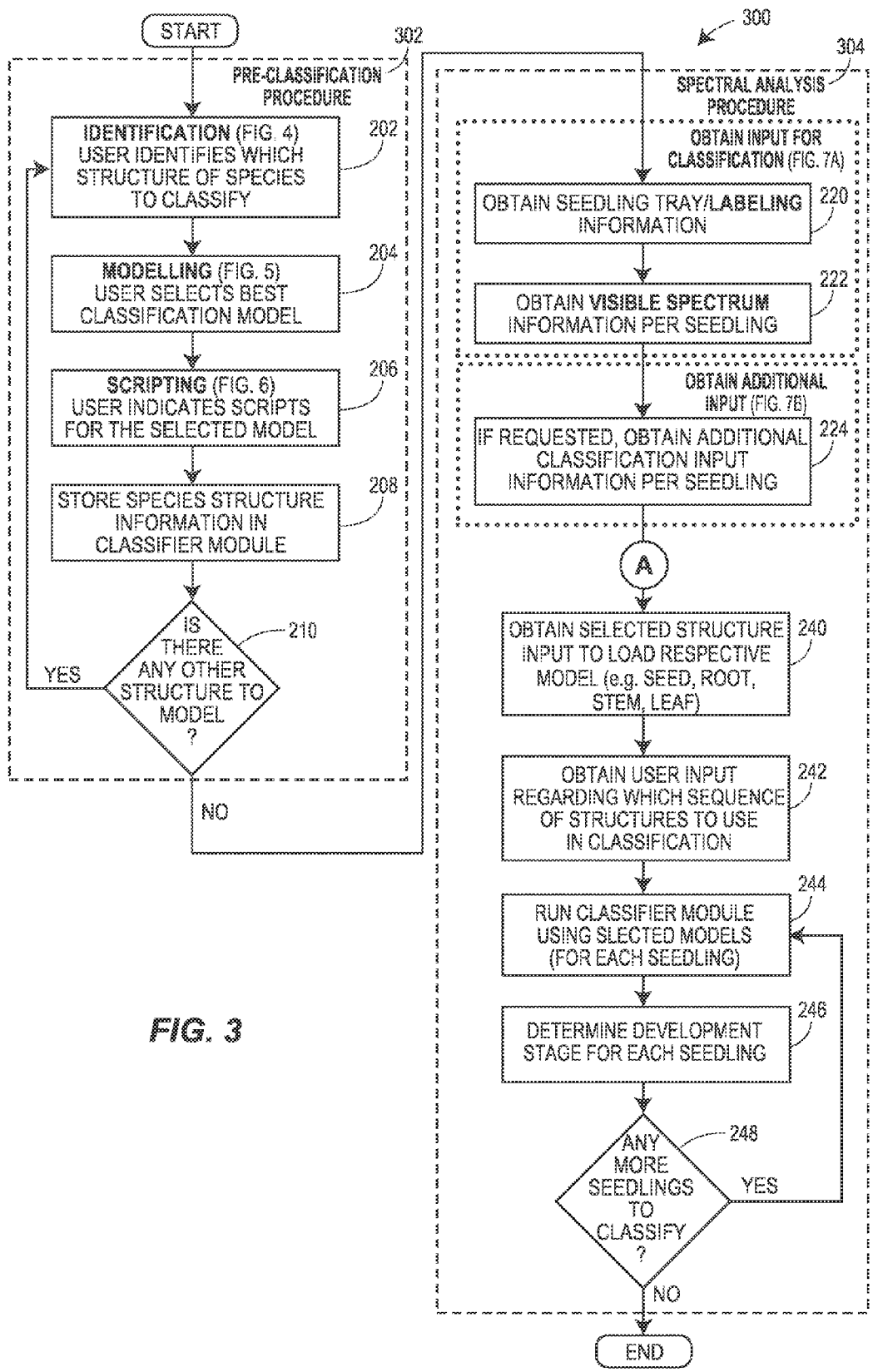
FIG. 3 is an exemplary flow diagram of a method of using spectral analysis to determine the existence of particular seed/seedling structures.

FIG. 3 illustrates an exemplary flow diagram of a method 300 of using an example pre-classification procedure 302 along with an example spectral analysis procedure 304 to identify the existence of a morphological structure of a seed. The classification procedure 302 and the spectral analysis procedure 304 may be performed by the system 200 of FIG. 2. For example, the user may use a modeling software module 122 (FIG. 2), such as Imap™ Database, Vision Module, Labview Vision Development Module 2010 produced by National Instruments, or other image analysis software, and a scripting software module 124 (FIG. 2), such as LabVIEW™ 2010, to perform the pre-classification section blocks 202-210.

For example, a user may obtain a red-blue-green image of a seed in a well, such as is illustrated (but shown in black and white only) in FIG. 11A. The scanner device 20 may use the first camera 30 to obtain the image and then the computer, e.g., PC2, may store that image for further processing. The user may view the image on PC2 using a modeling software module 122. The user may identify (block 202 in FIG. 3) which portion of a first red-blue-green image corresponds to a root structure of the seed in that image being analyzed. The user may identify part of the image data as being a root by using a graphical interface to draw a line around what the user identifies as the leaf. Other methods of selection are also contemplated as being included herein, but for purposes of practicality are not listed. Other seed structures, such as stem, root, seed coat, etc, may also be identified from the image data using the user identification process or any other process.

Figure 4:
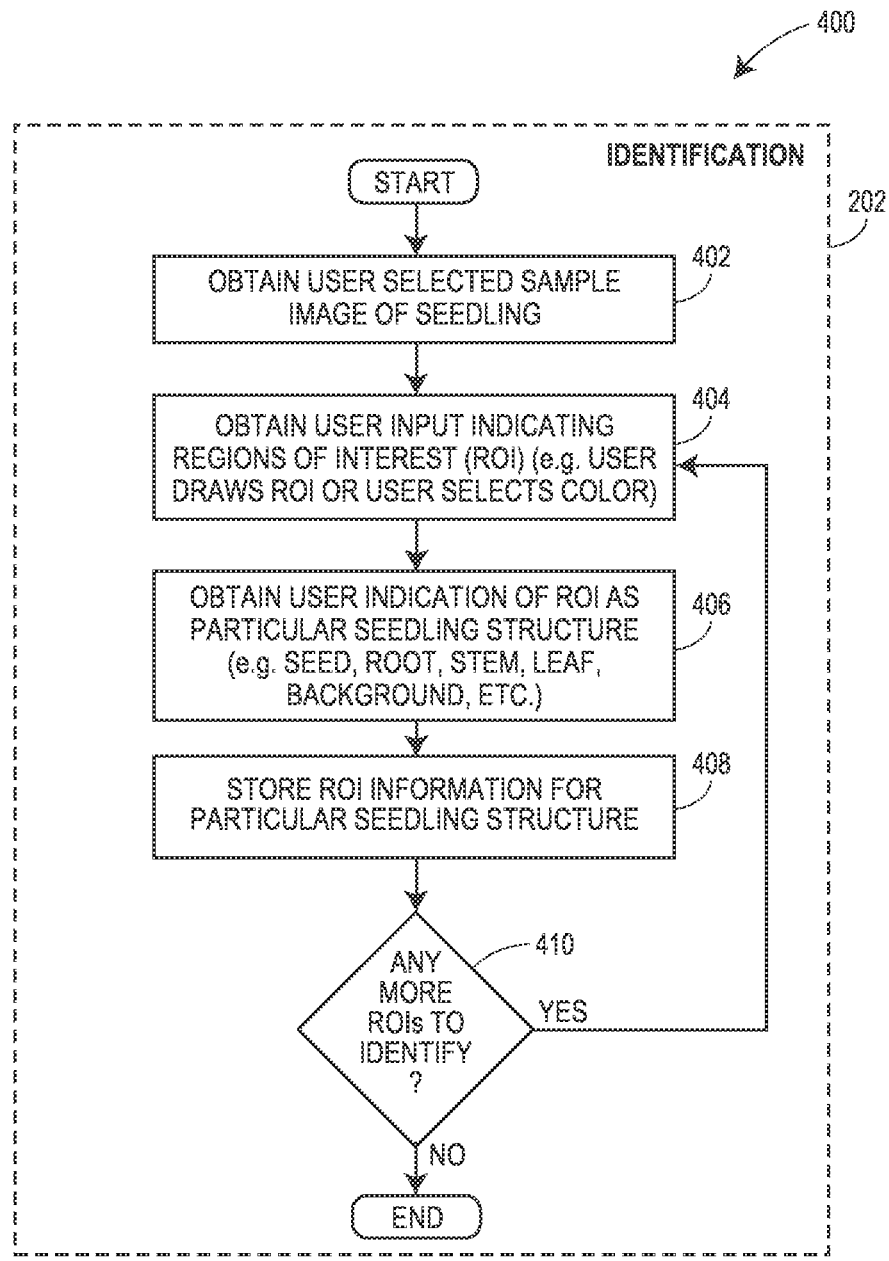
FIG. 4 is an exemplary flow diagram that provides an embodiment of the Identification block of the method of FIG. 3.

FIG. 4 describes an example user identification process 202 of FIG. 3 in greater detail. For example, the user may select an image to use in identification of a particular seed structure (block 402). The user may choose to identify the particular seed structure, e.g., seed coat, root, stem, leaf, etc. (block 404) as the region of interest (ROI) for submission to the modeling module 122. The user may select the selected region of interest (ROI) by using a graphical interface to draw a line around the image that the user defines as the particular seed structure (406).

Figure 12:
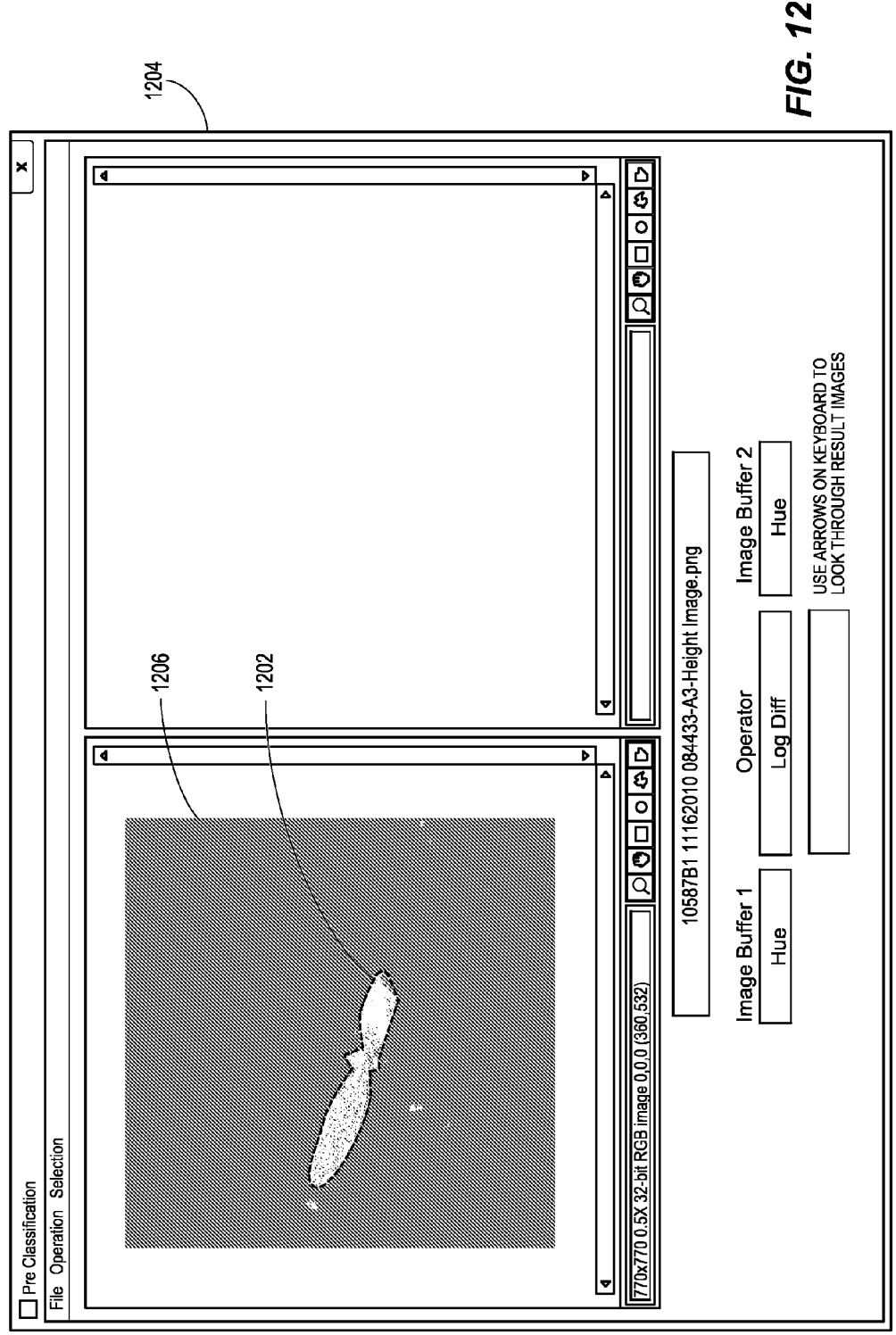
FIG. 12 illustrates an example of region of interest selection and a screen shot of an interface of the modeling module of FIG. 2 that may be used to perform the region of interest selection.

For example, as illustrated in FIG. 12, a user may use a user interface 1204 (e.g. a graphical user interface of the modeling module 122 of FIG. 2) to view a height determinative image input 1206, which may be used as a model image input. The user may use the modeling module 122 of FIG. 2 to make a region of interest (ROI) selection. The user may perform the particular seed structure selection by drawing a line around the structure which is to be used as the region of interest (ROI). FIG. 12 illustrates a line 1202 that a user drew around a leaf structure. This selection information may then be stored at the modeling module 122 (block 408). Thus, the leaf is the selected ROI, which will be later subjected for processing by the modeling module 122.

The user may be prompted to identify other structures (block 410). Otherwise, if there is no further structure for which a region of interest (ROI) is to be selected, the stored ROI/s (block 408) may be used as input by the modeling software module 122 (see block 240 of FIG. 3).

Figure 11C:
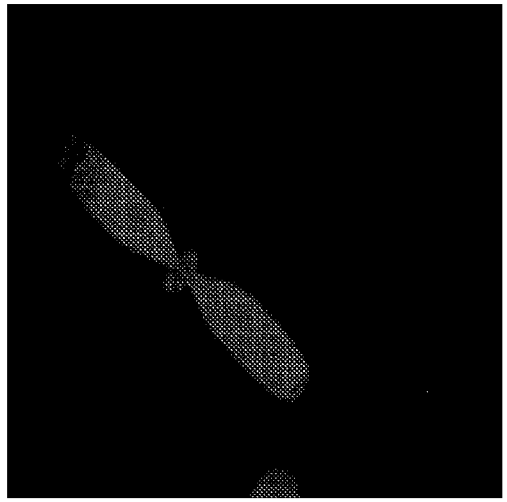
Figure 11B:
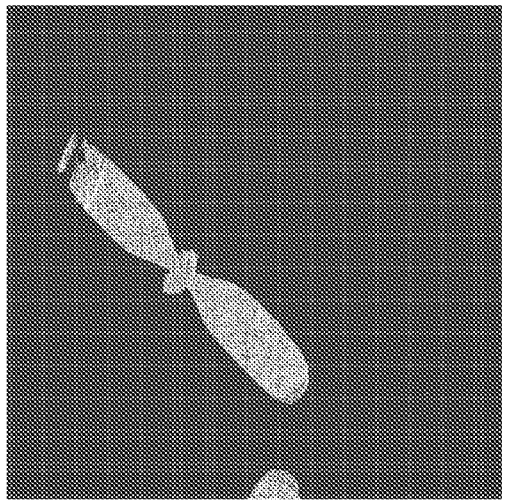

Alternatively, other image inputs may be used as a model image input instead of the example height determinative image input 1206 to start the identification process block 202. For example, any other image input, such as any one of the other spectral image inputs as illustrated in FIGS. 11A-11C (e.g., visual spectrum input (FIG. 11A); low chlorophyll input data (FIG. 11B); high chlorophyll input data (FIG. 11C)) or any other input data may be used as model image data.

Figure 21:
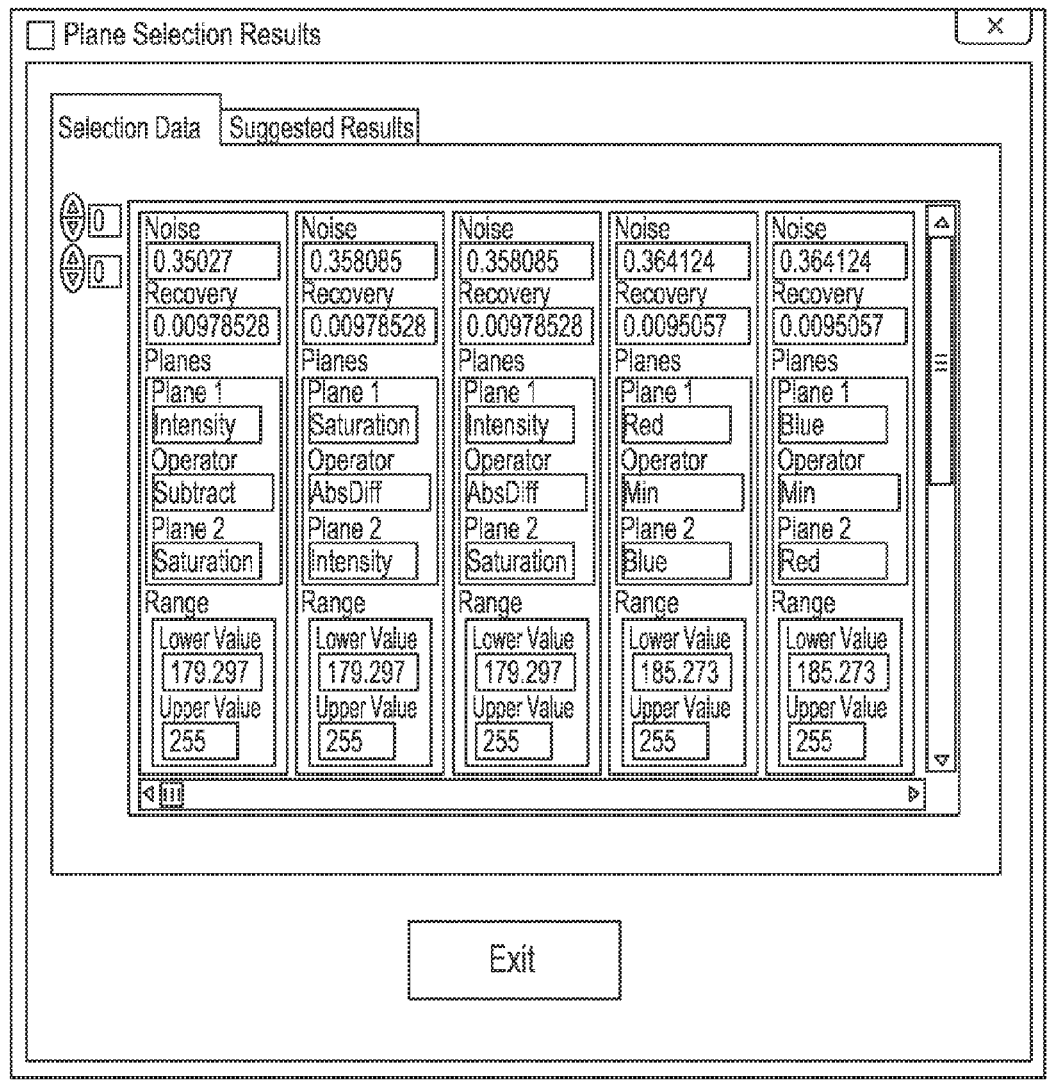
FIG. 21 illustrates an example of a portion of all of the results that may be provided by the modeling module, where the results list the parameter sets in an order of least amount of noise, so the user may more quickly come up with which parameter sets will work consistently in distinguishing the selected seed structure from the other image data for use in classification of the selected seed structure in other images.

The region of interest (ROI) that the user selected may be used to train the modeling software module 122 to produce a set of parameters that may best isolate similar seed from other similar input seed data images. The user may choose one or more sets from the resultant sets of parameters and then verify that at least one set of parameters works well at distinguishing the particular selected seed structure from the rest of the image data. FIG. 21, which is described in more detail below, illustrates an example of the resultant sets of parameters that may be produced by the modeling module 122.

Figure 5:
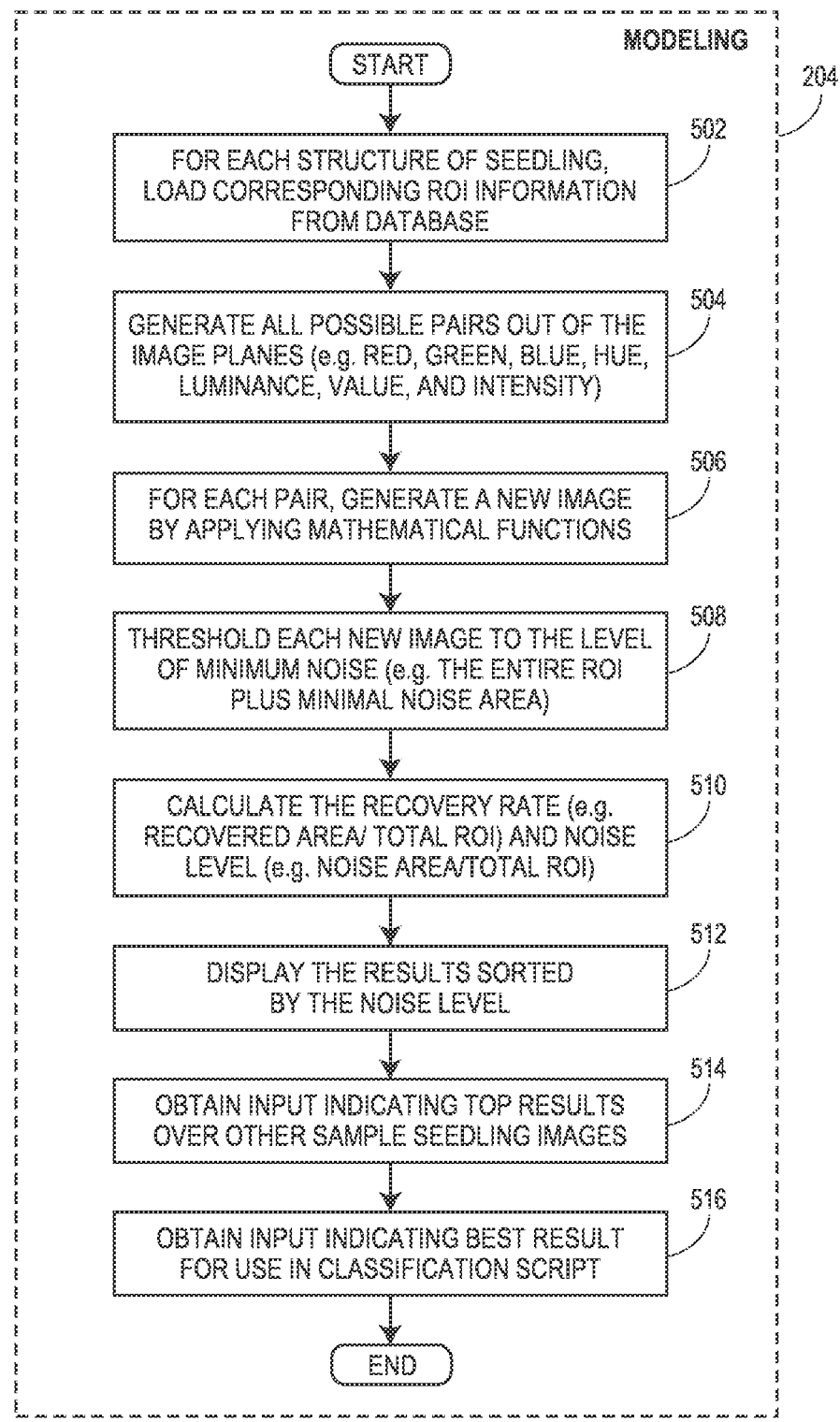
FIG. 5 is an exemplary flow diagram that provides an embodiment of the Modeling block of the method of FIG. 3.

FIG. 5 describes an example modeling process 204 of FIG. 3 in greater detail. For example, the modeling software module 122 may be loaded with the region of interest (ROI) information 1202 (from the model image data, e.g., 1206) that the user indicated (block 502) or that may be otherwise obtained (e.g., obtained from a database that may have stored region of interest selections per species structure, etc. and their respective model image data). The various parameters that may be analyzed by the modeling software module 122 include, for example, any combination of spectral information, such as any combination of red-green-blue image information plane data, such as: red, green, blue, hue, saturation, luminescence, value, and intensity. The modeling software module 122 may generate all possible pairs out of the image planes (block 504) from the obtained spectral information. The pairs of image planes are part of the set of parameters that may be selected for later use in classification. These plane parameters may be operated on by an operation parameter (1408) from a group of available operators, such as ADD, SUBTRACT, MULTIPLY, DIVIDE, MULTIPLY & DIVIDE, MODULO, ABSOLUTE DIFFERENCE, AND, NOT AND, OR, NOT OR, EXCLUSIVE OR, NOT EXCLUSIVE OR, LOGICAL DIFFERENCE, AVERAGE, MIN, MAX, CLEAR IF<, CLEAR IF<=, CLEAR IF=, CLEAR IF>, CLEAR IF>=, etc that may be used to produce the best distinction of the region of interest (ROI) selected seed structure from the particular information plane data. For each plane pair the modeling software module 122 may generate a new resultant image by applying an operator to the image plane pairs (block 506). The image plane pairs are information planes that may be obtained from the model image data.

The particular information plane data may be used to represent different respective information values that may range from 0 to 255 (or any other possible range depending upon the system 200 capabilities). The modeling software module 122 provides operators for use upon each of the planes of information in any combination with another plane/planes. The modeling software module 122 may be used to produce a set of modeling parameters that consistently and reliably produce the best distinction between the possible plane data sets in order to identify the particularly specified seed structure (e.g, leaf via ROI selection) from the rest of the image data, such as the background and other seed structures' image data.

Figure 14:
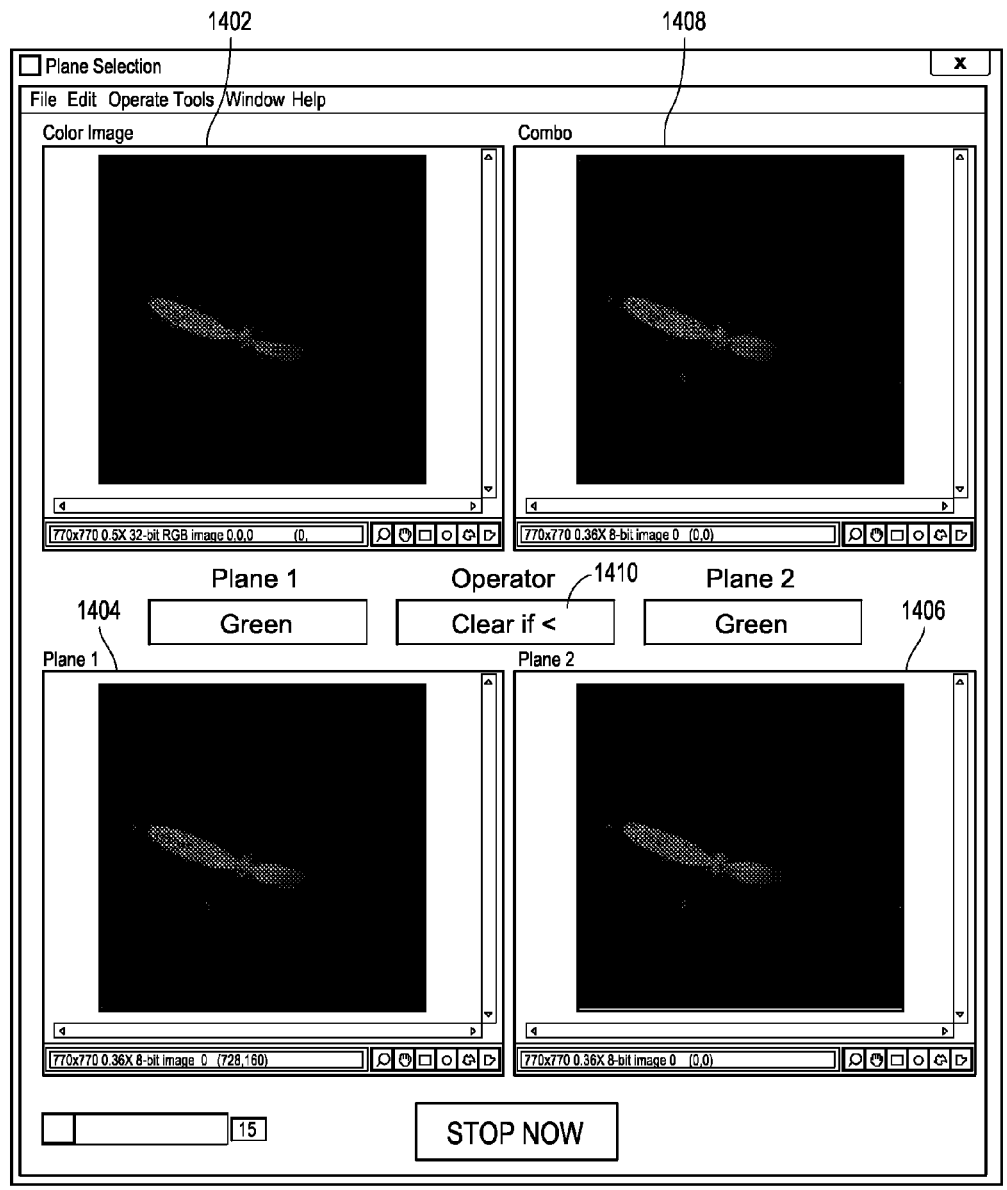
FIG. 14 illustrates an example user interface of a modeling software module.

FIG. 14 illustrates another example user interface (1400) of the modeling software module 122. The interface 1400 enables a user to select, view, and process different image planes by applying different operator parameters. For example, the "color image" (1402) is the original image obtained from a ccd type "camera 1" 30. "Plane 1" (1404) and "plane 2" images (1406) may be one of any plane image data from the example group of image data (e.g., red (R), green (G), blue (B), hue (H), saturation (S), intensity (I), (value) V, or luminescence (L), etc.) that may be extracted from the original color image (1402). The operation 1408 of "CLEAR IF<" may be used to create a combination image (1410) that may be used for later classification purposes. The modeling software module 122 may use the selected region of interest (ROI) information 1202 and a first image input as model image data 1206, such as the "color image" data 1402 to generate sets of modeling parameters that may best distinguish the selected ROI from the remaining image data. A user may choose one set of the parameters and compare the resultant image data 1410, which was produced using that set of parameters, with the original ROI selection to verify whether the particular set of parameters works well at identifying the corresponding ROI specified structure from the original input image 1402.

In the example illustrated in FIG. 14, the modeling software module 122 may have listed the set of modeling parameters which includes an extracted image plane GREEN out of the original color image and applied a "CLEAR IF<" operation to the corresponding pixels. For example, if a pixel value of the extracted GREEN (which is visible in 'plane 1' 1402) is less than the corresponding pixel value from the other extracted GREEN plane (which is visible in 'plane 2' 1406), then the value of the corresponding pixel in the combination image 1410 would be zero, i.e., would be black. Otherwise, the combination image may result in the green leaf structure as illustrated in 1408. The parameters shown in FIG. 14 is one set of the parameters of all the possible sets that the modeling software module 122 may check.

When processing each set of parameters, the modeling software module 122 records the noise level and recovery rate that results from each set of parameters compared to the user-selected seedling structure, e.g. ROI selection. Upon the completion of processing all the possible sets of parameters, the modeling software module 122 may summarize the records, sort them by noise level, and return the results for further selection by a user or for further processing by the module 122.

For example, the modeling software module 122 may produce some noise when applying a set of parameters to the input image. The noise may be reduced by thresholding the level of noise (block 508). The modeling software module 122 may further reduce noise by adjusting for noise by also taking into consideration the recovery rate information (block 510). The modeling software module 122 may be programmed to display the results sorted by noise level (block 512), and may also display the results of any noise adjustments.

FIG. 21 illustrates an example of a display of a portion of the results that may be provided by the modeling module (block 512), where the results list the parameter sets in an order of least amount of noise. With the noise information, the user or the modeling software module 122 may better determine which parameter sets may work more consistently in distinguishing the selected seed structure from the other image data. For example, a first resultant set of parameters, which are illustrated in FIG. 21, are "Intensity" "Subtract" "Saturation" with resultant image data in the threshold range of "179.297" to "255." The resultant image data may be called the combination image (e.g., 1408) or the "target" image data. The first example set of parameters produces a noise level of 0.350257, which indicates that the first example set of parameters produces noise of 35.0257% when these parameters are applied to the area that the user selected as the ROI. The next set of parameters produces 35.8085% noise, and so on. FIG. 21 also shows a recovery rate of 0.00978528 for the first set of parameters. In other words, the first set of parameters recovers 97.8% of the area of the ROI from the input image. These parameters may be selected for use in classification, or may be further adjusted.

The modeling software module 122 may verify that the resultant sets of model parameters are able to distinguish the ROI structure when applied to other sampled seed images (block 514), or a user may do this through trial and error. Based on the outcome of that verification for a group of different resultant sets of model parameters, a user, or the modeling software module 122, may select the best set of model parameters for use in the classification module (block 516) (for later use in classification e.g., at block 244 of FIG. 3). After a suitable set of model parameters is determined (block 204) by the user or the modeling software module 122, the pre-classification process may proceed to producing a classification script (block 206) based on the parameters and which script may be used for subsequent classification.

Figure 6:
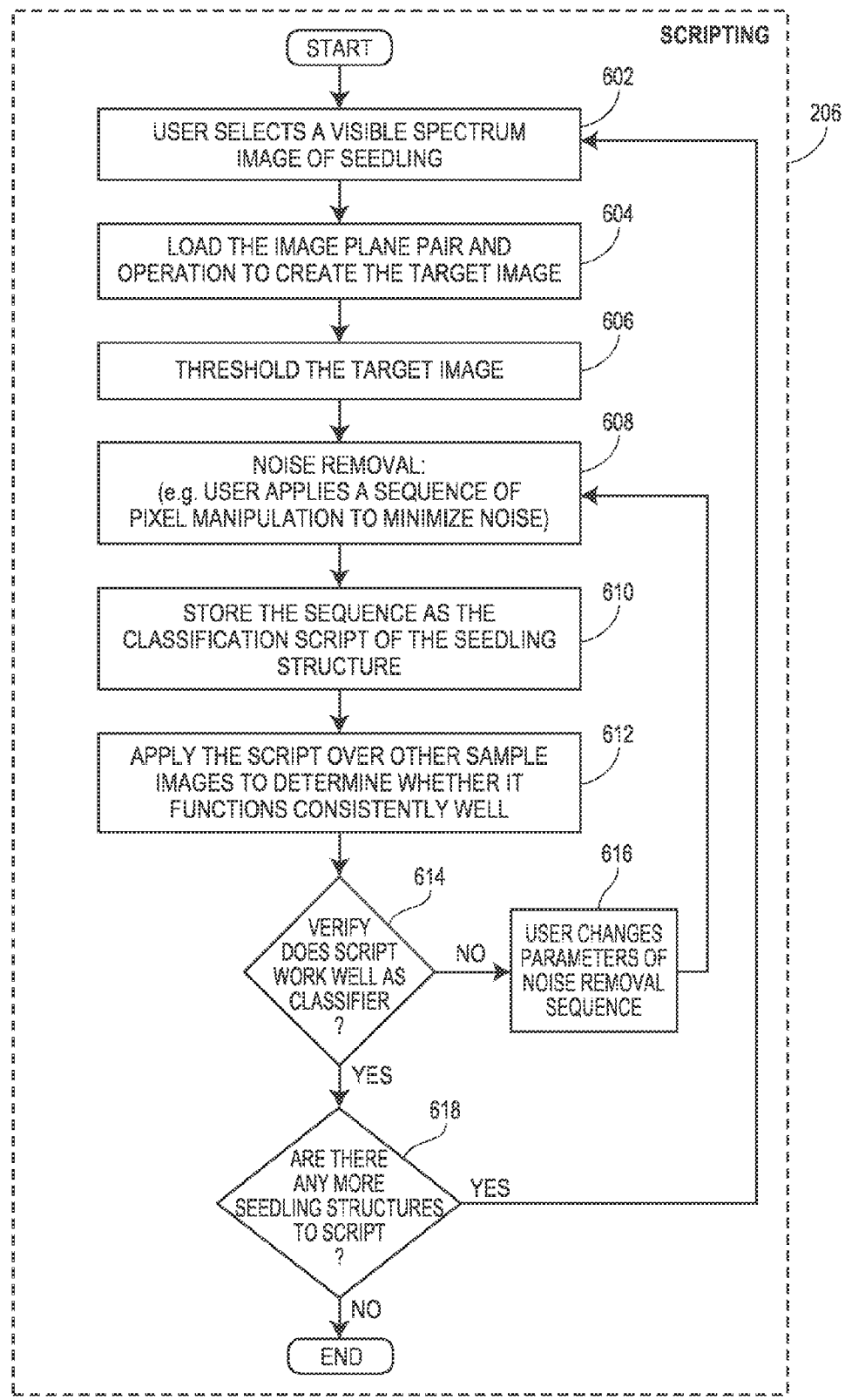
FIG. 6 is an exemplary flow diagram that provides an embodiment of the Scripting block of the method of FIG. 3.

FIG. 6 describes an example scripting process 206 of FIG. 3 in greater detail. A user selects a spectral image as the input image, for example the visible spectrum red-green-blue input image of the seed (block 602). The user may load the best resultant modeling parameters, such as the image plane pair, operation, and threshold level, e.g., the resultant modeling parameters produced by the modeling process (block 204) that create a target image that indicates the chosen set of parameters (block 604). With this target image, a user, or the modeling software module 122, may further define a specific seedling structure from all the other seedling structures by applying further thresholding, reversing, and/or noise removal techniques, if necessary, to produce another binary image in which only the particular seedling structure remains for other possible subsequent physical measurement/s. The user may use the selected, or further refined parameter information, as the corresponding target image (block 606). For example, additional noise removal may be performed by the user or the modeling module 122 by applying a sequence of pixel manipulation to minimize noise (block 608), such as dilation, erosion, and/or other commonly used binary operations. The user or the modeling module 122 may then store the final target data as a noise removal sequence that may be indicated as part of the classification script for the particular seed structure (block 610.)

The user may then manually, or the modeling module 122 may automatically, test and verify that the chosen classification script will positively and sufficiently identify a particular seed structure from the rest of the image data for subsequent images of different seeds (block 612). When the user or the modeling module 122 has verified that the modeling parameters work sufficiently and reliably, the user or the modeling module 122 may then select the chosen particular modeling parameters to be used by the classification module (block 614). Otherwise, the user or the modeling module 122 may adjust the parameters again to remove noise (block 616).

The scripting module software 124 may determine whether there are scripts to be produced for other seed structures (e.g., by prompting the user or reading code, etc.) (block 618). If there are no more structures for which to produce classification scripts, the process stores the seed structure classification scripts (block 208 of FIG. 3). Then the pre-classification process 302 may determine whether there are any other seed structures that require modeling by the pre-classification process (block 210 of FIG. 3).

The particular physical setup of the scanner devices and the conditions of the environment, such as the lighting in the room, will affect the light conditions that will in turn affect which particular parameters are suggested by the modeling module 122 of the pre-classification process that would produce the best modeling parameters. Therefore, the resultant set of modeling parameters may have to be recalibrated when the analysis is to be applied to a different system setup that would be subject to different lighting conditions. For example, a different light source.

After the pre-classification process is completed, by having produced the set of modeling parameters and their corresponding scripts, and the modeling parameters and scripts have been verified to be reliable for use in the automatic identification of seed structures, for example leaf structures, from a plurality of red green blue images, then the scripting module 124 may store the respective classification scripts (block 208 of FIG. 3). The scripting may be accomplished using any coding/scripting language, such as Labview™

For example, the associated species structure information, such as which species (e.g., pansy seed) and which structure thereof (e.g., leaf, root) was identified, and with which set of modeling parameters (e.g., "AND-ing the blue and saturation planes") were used to produce which modeling classification script (e.g., see FIG. 13) are then stored in the classifier module 126 (block 208 of FIG. 3) for later use. An example of seed structure scripts that may produce a resultant classification image (e.g., FIG. 17C-D) is illustrated in FIG. 13.

FIG. 13 illustrates example scripts that may be used to distinguish the following portions of a seedling input image: the background, the whole seedling structure, the leaves, the stem, the root and the seed coat for a pansy seed.

The pre-classification process 302 may check if there are any other seed structures to be modeled (block 210). If there are more structures to be modeled, then the process may go through blocks 202-208 again for identifying, modeling, scripting, and storing seed structure classification script information for another seed structure, such as stem, leaf, seed coat, etc. If not, then the pre-classification process 302 is completed, and then the overall method of using spectral analysis to identify seed structures 300 may proceed to do more automatic subsequent analysis of other seeds.

The subsequent analysis of other seeds of the process 300 may proceed by obtaining the labeling and spectral information input (block 220) of other seeds. The pre-classification process produces scripts that may be used to automate the subsequent analysis of individual seeds in conjunction with further processing.

Alternatively, the pre-classification process 302 may cease with the production of the scripts that are required for later automatic analysis. For example, the pre-classification process 302 may be accomplished at one time, and at a later time the scripts produced by the pre-classification process 302 may be used to analyze similar seeds of a group by subjecting each of those seeds to a later analysis of only a single spectral analysis procedure or a multiple spectral analysis procedure. The automatic analysis may be based on the particular model parameters that were determined in the pre-classification process. After the pre-classification process has generated the scripts, an automatic classification process may use the scripts to analyze each individual seed of a plurality of seeds that are set up for automatic classification using the example seed analysis system 200.

Blocks 220-248 of FIG. 3 describe the automatic analysis process that may use the classification scripts that were generated by the pre-classification process 302 (e.g., blocks 202-210). The automated analysis process may begin by obtaining seed identifying input that identifies what kind of seed is to be analyzed (block 220). Then the scanner module 110 may obtain the at least one particular spectrum input that is needed to classify the particular seed (block 222). If the classifier module 120 determines that additional spectral input is required, then the additional spectral input may be obtained (block 224).

Whether additional spectral input is required is dependent upon what classification the user is interested in obtaining. For example, a simple seed analysis may use the script obtained from the pre-classification process to subject a pansy seed to determine whether or not a root structure has formed so that the individual seed may be classified as such. In another example, the pansy seed may be subjected to analysis of all its structures, for example determining whether a root, stem, or leaf is detectable.

All the structures of the pansy leaf may be detectable using only a single spectral input, which would have been used to identify all the seed structures using the modeling, and scripting procedures, e.g., 204 and 206. Alternatively, the pansy seed may be subjected to additional spectral analysis by, for example, having the seed subjected to any one or more of a low-chlorophyll laser, a high chlorophyll laser, a height triangulation laser, low frequency laser, high frequency laser. The laser may produce different signal wavelengths that correspond to the photosynthetically active radiation (PAR) region that photosynthetic organisms are able to use in the process of photosynthesis, etc. (block 224).

Figure 7A:
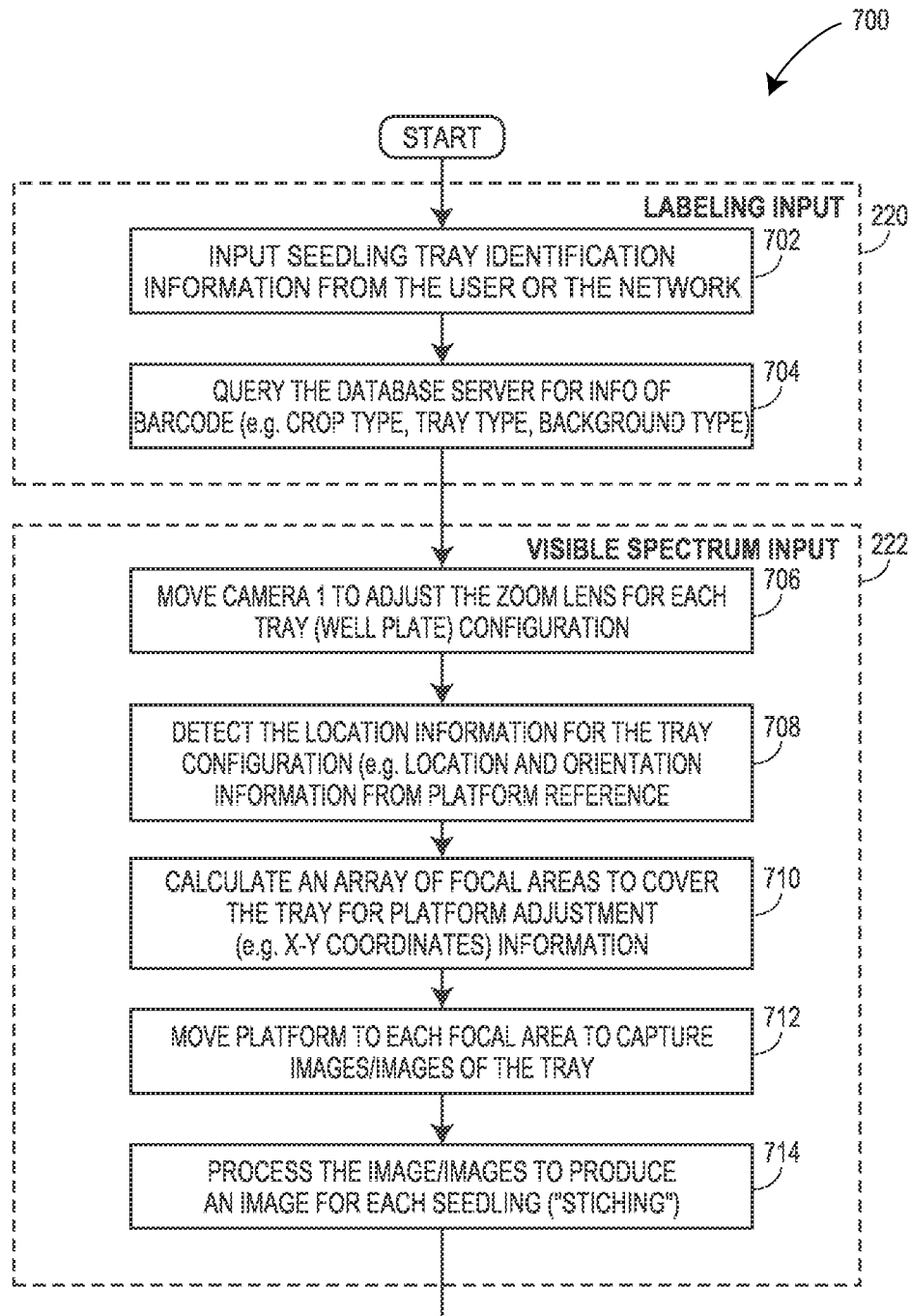
FIG. 7A-7B are exemplary flow diagrams that provide embodiments of the Classification blocks of the method of FIG. 3.

As may be used by the subsequent automatic analysis of seed structures, FIG. 7A describes an example labeling input process 220 in greater detail. For example, seed information may be obtained automatically by having the robot 10 and scanner device work together to obtain, for example, seedling tray information, which may be labeled on each tray 6, or a user may input the information via an input device (not shown), such as a handheld scanner that may read an RFID chip or a bar code (e.g., a linear or 1-dimensional, 2-dimensional, 3-dimensional, etc., bar code), or the user may input the information via another type of input device, such as a keypad, or wireless device (block 702). The labeled information may include information such as what species of seed is being analyzed, which batch the seed is from, and any other type of information that is useful for managing the process. The classifier module 120 may obtain the required information from any storage location of the system 200 (block 704). For example, the labeling information may be stored at the handheld scanner software (not shown), which may be coupled or ported to the storage of the classifier module 22, which may have storage distributed to its modeling module 122 and/or classification module 126.

Using the particular seed type information, the robot 10 and scanner device 20 may coordinate with the scheduler module 22, the robot module 12, the scanner module 110, and the classifier module 120 to obtain image data of the remaining respective seeds to be classified (block 222) from that particular well plate 4, as well as all other well plates being processed for analysis in that given run.

FIG. 7A also describes, in greater detail, an example of the process for obtaining an example first type of spectral input, such as a visible spectrum input per seed 222. For example, after the tray 6 was scanned for the seed labeling information, the tray 6 may be placed onto the platform stage 80 for automatic seed structure analysis. To perform the automatic seed structure analysis, the camera 30 may be moved to capture an image at a different x-y location over the tray 6 and may be moved in a different z direction to focus properly over the different x-y location (block 706). Alternatively, the platform stage 22 may be moved in the x-y-z directions or any rotational or other combination of references.

The scanner module 110 may identify the tray location and orientation on the platform stage. (block 708) With the location and orientation information, the scanner module 120 may calculate one or more focal areas with which to determine how to obtain images that span the tray 6 (block 710). The classifier module 120 may direct the camera 30 to move in order to focus on different locations of the tray 6 to produce one or more images of the tray. The scanner module 110 may also direct the platform stage 22 to move to adjust the tray 6 so that images may be captured at each of the one or more focal areas (block 712). Depending upon how many focal areas were determined, for example eight focal areas per a tray of twenty-four wells, the scanner module 120 may process the eight images to produce individual seed-well images (block 714). At this stage, the process 300 may stop from obtaining additional input, and then proceed to block 240, where the process continues the analysis of the individual seeds in the respective wells based solely on information obtained from a single spectral input.

The method 300 may include capturing additional spectral analysis information (block 224) per tray 6, or other unit. The additional information may include capturing other spectral inputs, such as any one or more of the following spectral inputs: low-level chlorophyll data, high-level chlorophyll data, height data.

After the scanner module 110 captures and stores the seed data for automatic classification per any unit, such as, per tray, or per well, etc., the system 200 may cause the classifier module 126 to obtain the stored seed data from the scanner module 110 (block 240). The method 300 may have the classifier module 110 automatically load the associated modeling script or may prompt the user (block 242) to select which structures to use to classify the seed images.

Figures 17A, 17C:
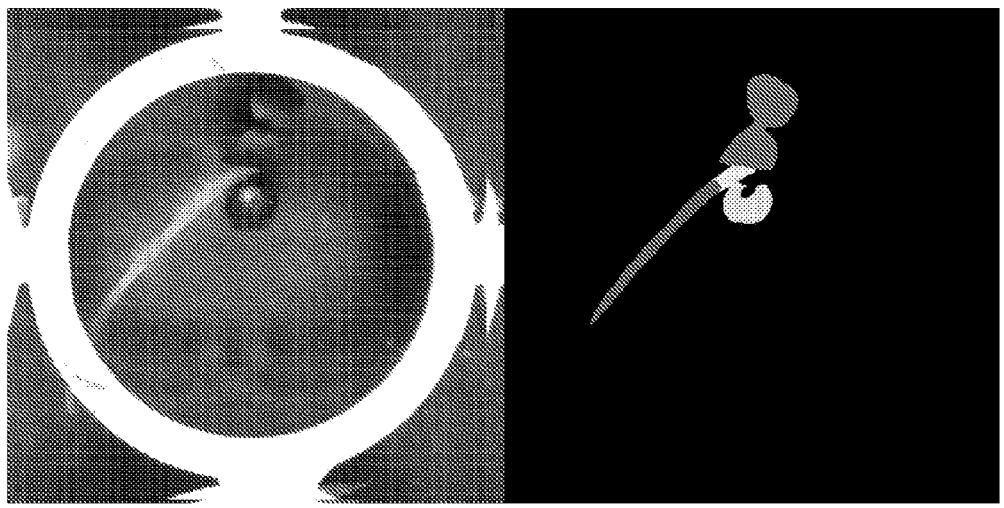
FIGS. 17A-17D illustrate an example of an initial image capture and a final classification image that may indicate where each particular seed structure was identified by using different colors to indicate the existence of the particular structure.
Figures 17B, 17D:
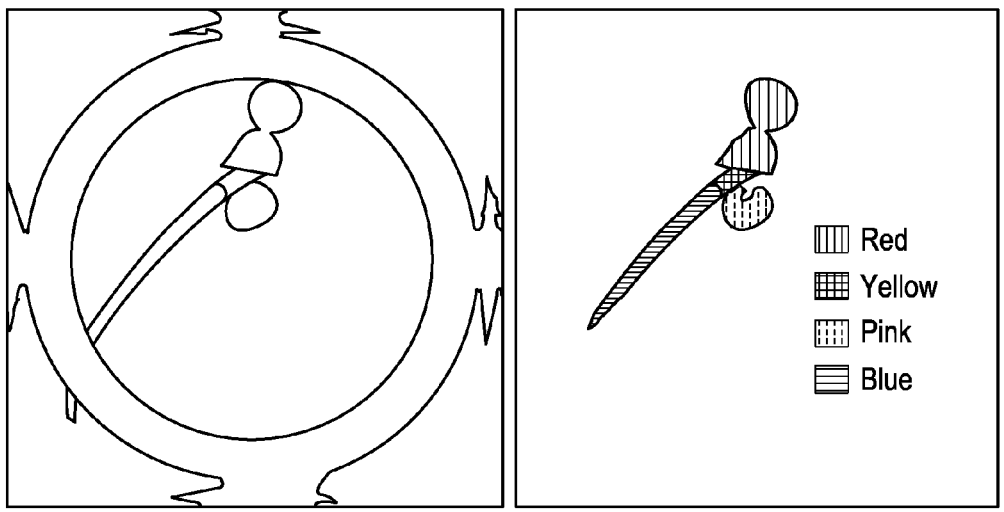

The individual seed images of the remaining seeds may be analyzed by the classification module 126 (block 244) to produce a final image of the individual seed. The final image of the individual seed may be a composite image that indicates if and what portion of the image that is classified indicates any one or more of the seed structures, (e.g. seed coat, slip, root, hook, stem, leaf, etc.) For example, FIGS. 17A and 17C illustrate, respectively, an example of an initial color image capture and a final color classified image that may indicate where each particular seed structure was identified by using different colors to indicate the existence of the particular structure. FIGS. 17B and 17D illustrate, respectively, the color images of FIG. 17A and FIG. 17C in black and white, with shading indicating the colored identified seed structure regions.

The classifier module 120 may then determine which developmental stage the individual seed has reached based on the determination of which seed structures were found to exist in the seed. The classifier module 120 may make the classification determination using only a single image that was produced using a single spectral input based upon any number of pre-determined classification scripts (block 246). Alternatively, the classifier module 120 may make the classification determination using multiple images that were produced using multiple spectral inputs (block 246). The classifier module 120 may produce a resultant classification image that identifies where each seed structure or sub-structures was found in the original input image/s (e.g., FIG. 17D) along with any other type of output, such as a simple germination stage determination per seed.

The classifier module 120 may make a classification determination based on whether multiple structures of a seed are existent per seed, and then run the same classification routine to classify the next seed of a batch (block 248). Alternatively, the classifier module 120 may classify one structure per seed at a time. For example, the classifier module 120 may continue analyzing each seed image for a single structure before moving to classify the next seed structure for the batch of seeds. No matter the order of processing, the end result is to determine a classification for each seed based on the existence or non-existence of one or more selected seed structures, such as a morphological seed structure, and/or a physical measurement of any of the seed structures.

For example, a simple classification procedure of method 300 may include the above-described process including the identification, modeling, scripting, and storing performed for a pansy seed leaf structure. The pansy seed may have only been subjected to a single spectral input that would produce a single image recording of a red-green-blue image with the first camera 30. There may be no need to obtain any additional classification input (i.e., the omission of block 224 of FIG. 3). For example, if the only selected seed structure for classification was the root, then subsequently analyzed seeds may be classified as either having or missing a leaf.

Otherwise, the scanner module 110 may obtain additional spectral input data (block 224) by using seed analysis system 200 of FIG. 2. For example, the first camera 30 is described above as being used to obtain a first spectral input, e.g., a red-green-blue image of the seed. The second camera 40 may be used to obtain a second spectral input, e.g., reflection data that is captured by subjecting the seed to a first laser 50 and/or second laser 60. The first laser 50 may be set to produce a 650 nm signal and have settings that may be chosen from 0 to 10 kHZ. The first laser 50 and second laser 60 may be run respectively at 1.5 kHz for low chlorophyll analysis and 8 kHz for high chlorophyll analysis. The seed may be subjected to the laser 50 and the reflection may be recorded by second camera 40. The details of this embodiment that requires additional spectral input is described below with reference to the embodiment illustrated in FIG. 7B.

If a second spectral input is required, then the classifier module 120, may also have associated script data that was obtained with the corresponding above described pre-classification process, which includes identification, (block 202), modeling (block 204), and scripting (block 206) that were executed in association with the second spectral input. If a second spectral input is required, then classification module 126 may load the corresponding classification scripts (block 240) in addition to the classification script that was associated with the first spectral input.

At this stage, the user may be prompted for a selection of the available classification scripts to use in classifying the seed (block 244). Alternatively, the classification scripts may be pre-determined based on the seed labeling input that was obtained at block 220. Regardless, the classification module will run the analysis of the particular seed using the respective classification scripts (block 244) in accordance with which type of spectral inputs are required.

The classification scripts may establish which seed structures are present from the one or more spectral input data that was obtained with the example seed analysis system 200. Therefore, the classification of each seed may be determined (block 246). The automated analysis system 200 may run the classification module until there are no more seeds remaining per particular seed batch (block 248). While the embodiments herein describe a particular order to the block operations, the order of the steps may be reconfigured and still be in accordance with embodiments of the invention. For example, there may be multiple ways to remove noise for a specific seedling structure, but still remain within the scope of the disclosure.

Figure 7B:
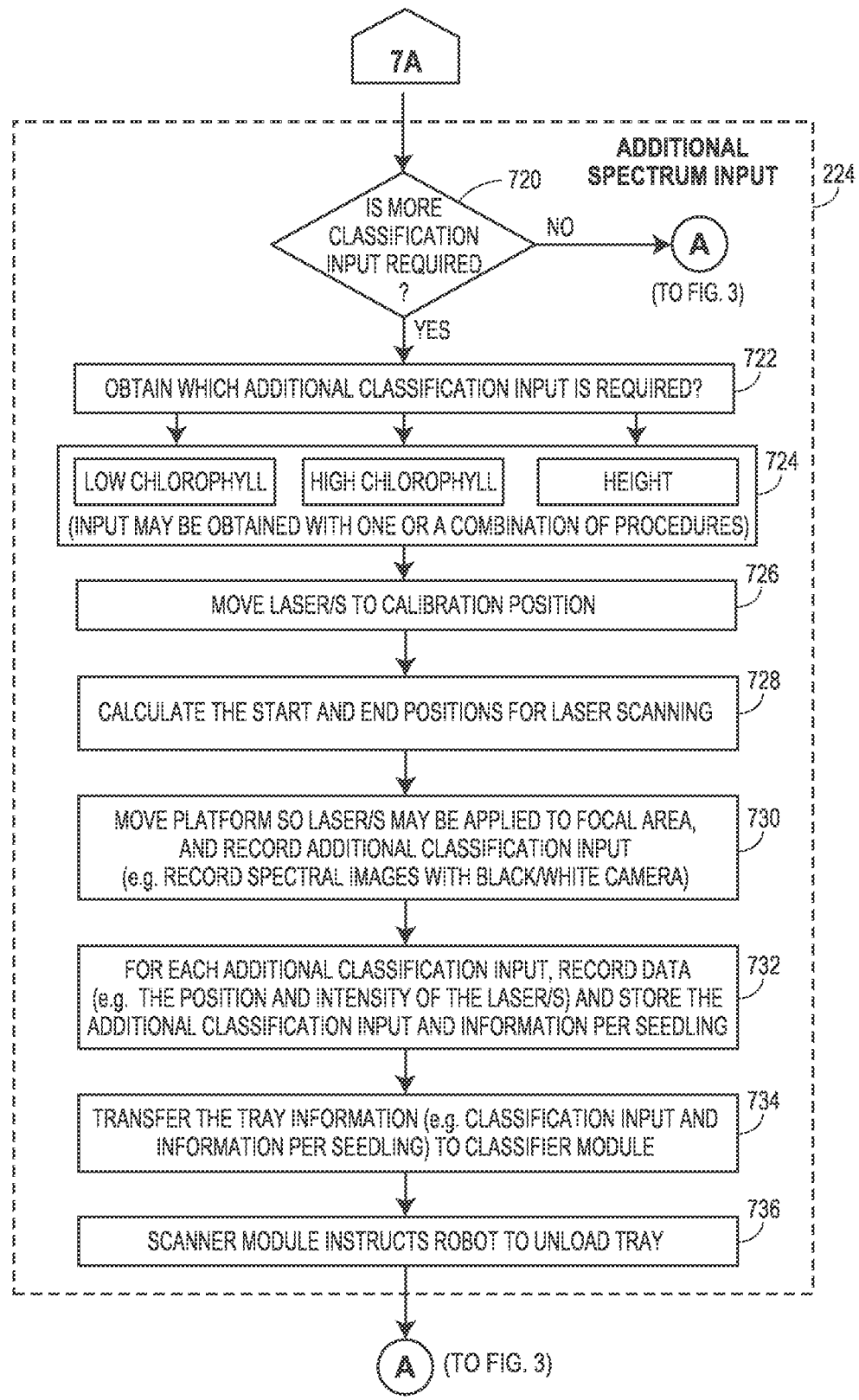

As described above, FIG. 7B provides details of an embodiment of obtaining additional spectral input (block 224). For example, as illustrated in FIG. 7B, if more than one spectral input is required (block 720), the classification module 126, may determine which additional input is required (block 722). For example, the classification module 126 may make the determination by prompting a user, or it may determine the additional spectral input that is required based on the information obtained by the seed analysis system 200 at block 220 when, for example, reading a bar scan label on the seed tray 6.

Referring to FIG. 2 and FIG. 7, if, for example, the additional spectral input that is required is going to be used to classify a pansy seed as having any or all of the seed structures, such as a root, a stem, and a leaf, then the following are a combination of additional spectral inputs that may be obtained: low chlorophyll reflection data, high chlorophyll reflection data, and laser triangulation height data (block 724). To obtain the additional spectral input, both lasers are modulated at the same time to the low level frequency (1.5 kHz). Images are recorded. Then both lasers are modulated to the high frequency (8.5 kHz) and more images are recorded.

As example of a recorded image obtained by submitting the individual seed to a low chlorophyll laser is illustrated in FIG. 11C. Generally, the image illustrated in FIG. 11C should show the leaf structure. Generally, the image illustrated in FIG. 11B should show a combination of the leaf and stem structures.

Figure 15A:
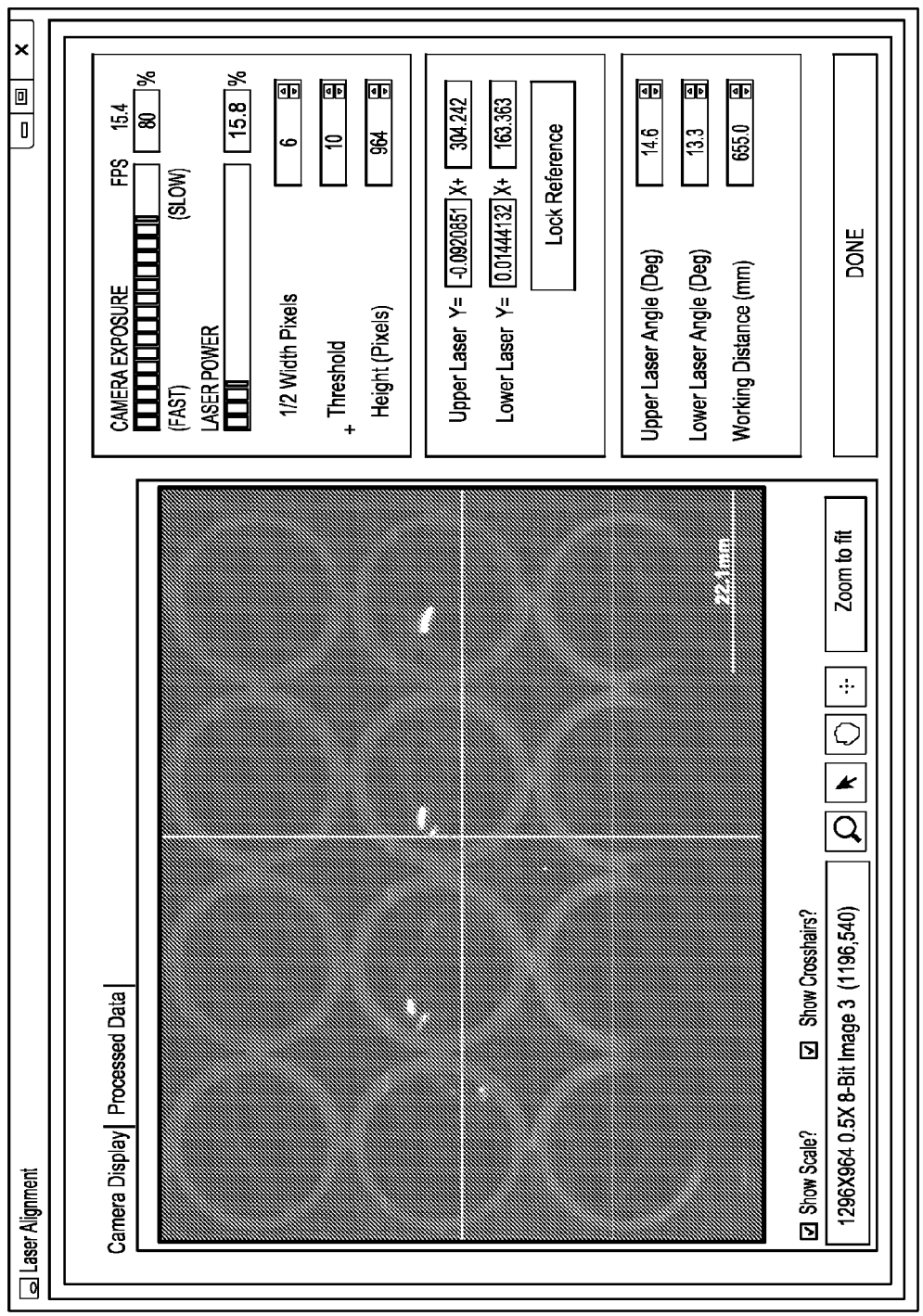
FIG. 15A-15B illustrate another example of multi-spectral image inputs for use in classification processing.
Figure 15B:
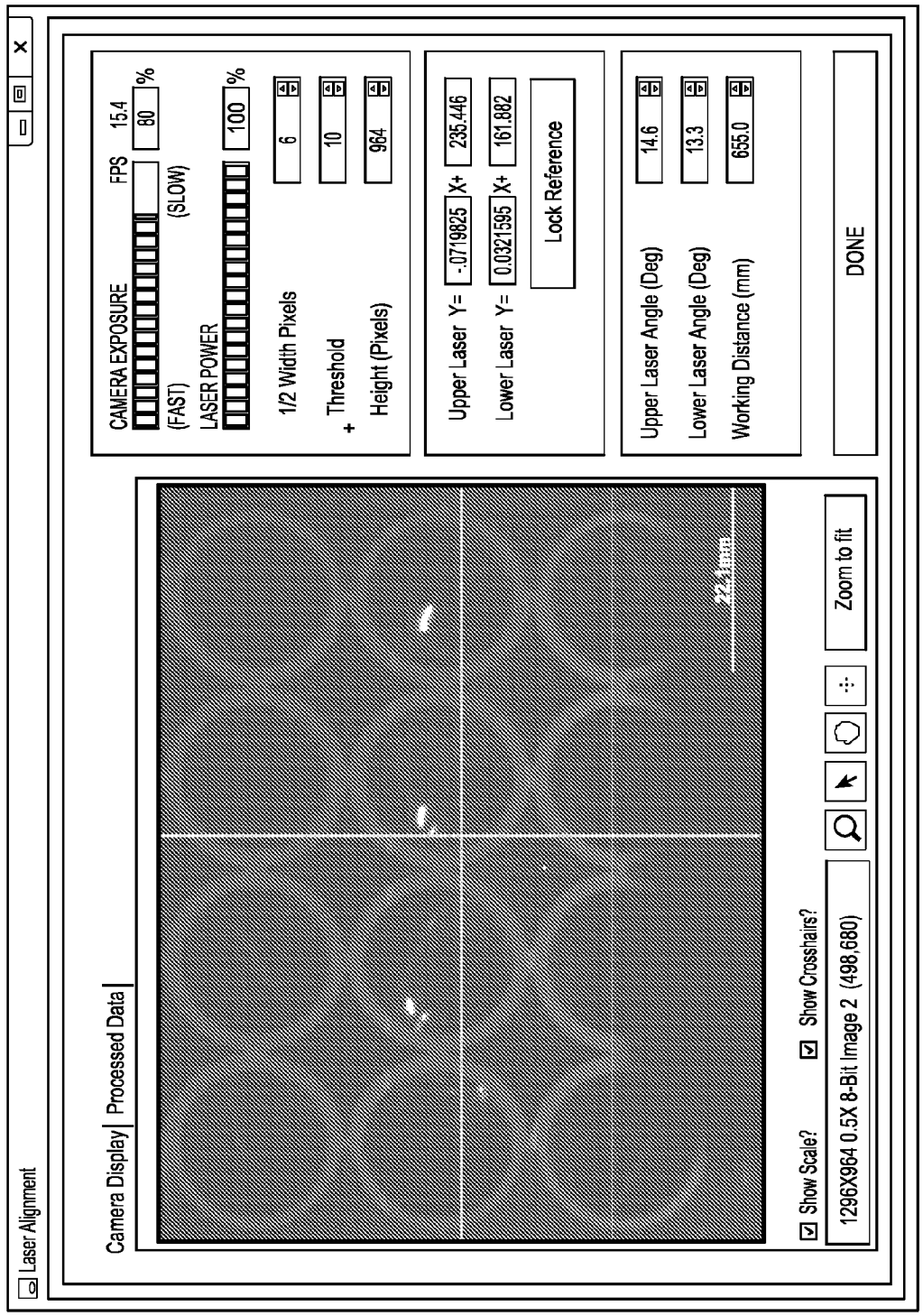

FIG. 15A-15B illustrate another example of a low-chlorophyll laser (e.g., a laser set at 15% power) produced image (15A) and a high-chlorophyll laser (e.g., a laser set at 80% power) produced image (15B). From the images of FIGS. 15A and 15B it is easier to visibly distinguish the leaf from the stem as the leaf shows up stronger in the high-chlorophyll laser produced image (15B).

In either case, the classifier module 120 may determine whether a stem or leaf exists by subtracting data from the low-chlorophyll laser signal image data from the high-chlorophyll laser signal image data. For example, what remains after the subtraction would be an indication of the existence of a stem, and what is removed may be an indication of the existence of a leaf. Therefore, the seed may be classified as either having a stem or both a leaf and stem.

For cost reduction and efficiency purposes the system 200 may use the second camera 40 to record both of the example additional spectral inputs (e.g., high-chlorophyll reflection input and the low-chlorophyll reflection input) simultaneously by having both the first laser 50 and the second laser 60 simultaneously apply signals across the seed location in its respective well. The scanner module 110 and/or classifier module 120 may coordinate the processing of the high-chlorophyll reflection input and the low-chlorophyll reflection input in to be recorded by a single second camera 40 during a single movement of the tray 6. In order to record both additional spectral inputs with the single camera 40 each individual seed of the tray 6 may move into the camera's 40 focal point in accordance with blocks 726-736, which describe example details of how to obtain the additional multiple spectral inputs simultaneously with one camera 40.

Figure 16:
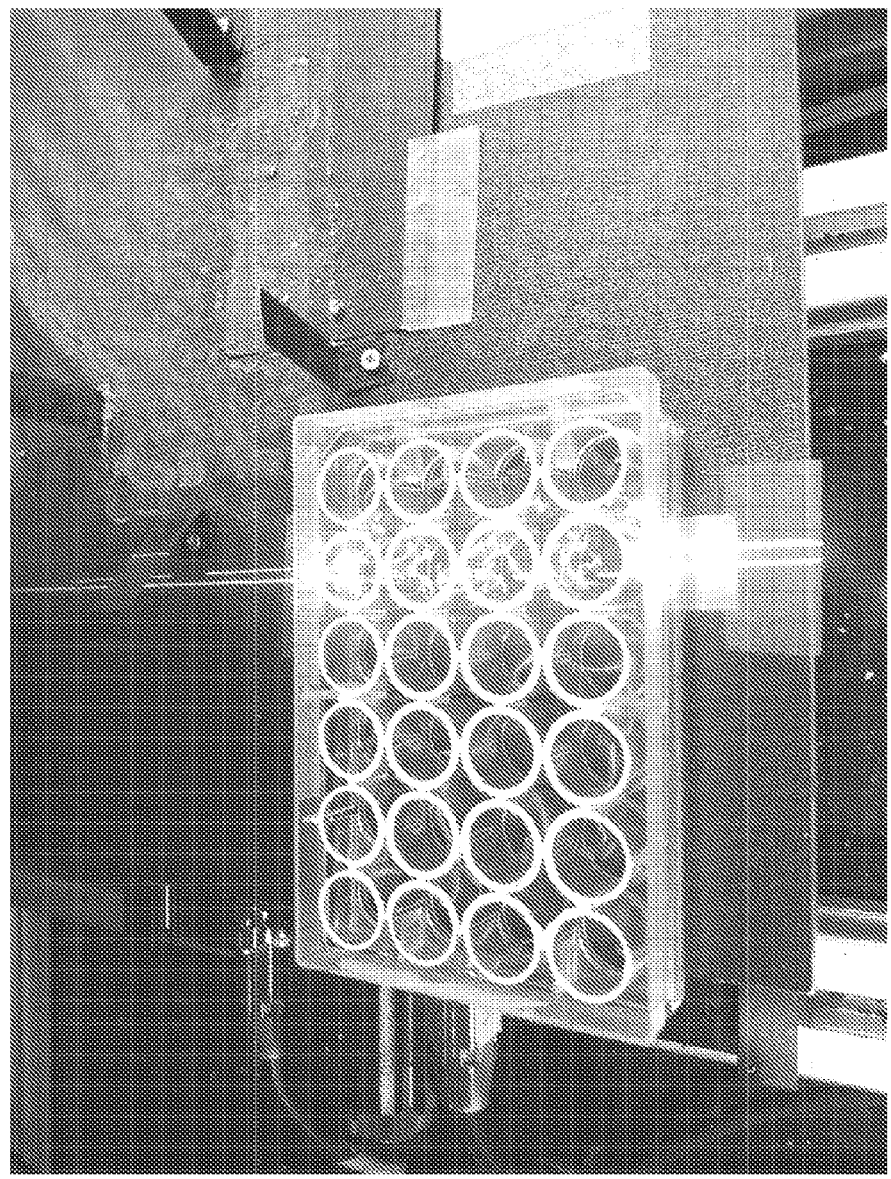
FIG. 16 illustrates an example of a method and apparatus for submitting the seed in the well of FIG. 1 to simultaneous laser signals from the lasers of FIG. 2.

For example, the system 200 may be fixed to take advantage of the physical characteristics of its components. For example, FIG. 16 illustrates how the vertical sides of the well are used as a physical barrier that acts in conjunction with an offset angle from the x-z plane formed by the of the two laser signals. With the example configuration of FIG. 16, the scanner module is able to record both of the laser signal reflections at different times to produce the two separate reflective images, based on e.g., high-chlorophyll reflection input and the low-chlorophyll reflection input. As describe above, an example of a high-chlorophyll image is illustrated in FIG. 11B and an example of a low-chlorophyll image is illustrated in FIG. 11A.

FIG. 7B describes more details of an example process for obtaining additional spectral input. For example, one way to acquire the additional spectral input is to adjust the lasers 50, 60 to a calibrated position, such as is discussed above, e.g., having the two lasers offset by an angle in the x-z plane from the z-axis (block 726). The scanner module 110 may then calculate the start and end positions for recording the reflected laser signals (block 728). Each laser may produce a line signal that stretches in the y-axis direction as is seen in FIG. 16. Thus, the recording may only occur when the well is passing through calculated start and end positions (block 728). The scanner module 110 may then record the two additional spectral reflection inputs while the platform stage moves the seed into the focal region (block 730) so that the respective line recordings may be processed to form two respective complete images of the detected seed structures (block 732). After the recording is completed, the scanner module 110 may record and store the additional data for each seed (block 732). The scanner module 110 may then transfer the additional spectral input images associated with each seed to the classifier module 120.

For example, the scanner module 110 may control the platform stage to move in the x direction. The well 2, which holds the individual seed 1, has a vertical wall that forms two sides along the x-axis, and the two sides have a certain height. The first laser 50 and the second laser 60 may be configured at opposite angles from the z-y plane so that the first laser 50 will produce a reflection as the well travels across the x-direction in a plane that is perpendicular to the y-z plane. The height of the side of the well on the right side as depicted in FIG. 2 (positive x-axis side) will block the signal from the second laser 60 while the first laser is applied to the seed so that both lasers will produce reflection data as the plate travels under the field of view.

Thus, for example, the first image captured by the second camera 40 will be the image reflected from the signal produced by the first laser 30. The scanner module 110 will direct the platform stage 80 to move in the x direction so that the well travels a distance in the x direction to a point where the second laser signal is not blocked by a side of the well, and thus is able to reflect back to the second camera 40. In this way, both laser reflection data from each laser 50, 60 may be obtained with a single pass of the platform stage 80 in the x-axis direction. Alternative methods of obtaining the additional spectrum input data are included by the embodiments, such as using other light spectrums such as ultraviolet or near infra-red.

The above detailed example embodiments do not limit the disclosure, but are presented to satisfy current written description and enablement requirements of U.S. patent law.

More generally, embodiments described herein either: (1) employ a pre-classification process to produce classification scripts that are used with a process of obtaining a single spectral input, which are used by a classifier module to determine which seed structures exist in order to determine a classification for a particular seed, or (2) use already generated classification scripts that were generated by a pre-classification process in combination with a process of obtaining a single spectral input, which are used by a classifier module to determine which seed structures exist in order to determine a classification for a particular seed, or (3) already generated classification scripts that were generated by a pre-classification process along with a process of obtaining a plurality of different spectral inputs, which are used by a classifier module to determine which seed structures exist in order to determine a classification for a particular seed.

Example Applications that May be Integrated with Embodiments

Any such classification procedure may be used for purposes of later commercial use or sale of the seed or the seed lot from which the seed was chosen. For example, classification of a large group of seeds may be required. To classify the group of seeds, a sample group may be selected, and each of the individual seeds from the sample group may be run through the example classification procedures described herein to determine which seed structure/s are present in each seed. Depending upon the determination, for example, if each or many of the seeds of the sample group have been determined to have a root, stem, and leaf, then this information would translate into information that the seed lot from which these seeds came has a very good percent germination.

A critical characteristic of seed lots is "percent germination," meaning the percentage of seed which will germinate and develop into normal seedlings. This information is necessary for virtually all commerce in seed and for planning how much seed is to be sown to result in the required number of plants. Further, as seeds deteriorate over time, percent germination of a given seed lot must be determined periodically. Thus, germination testing is an important and widely practiced function. In many jurisdictions, testing methodologies are specified, minimum germination standards enforced, and government-run testing laboratories are active.

Germination testing is typically performed in specially-equipped laboratories by trained personnel. A sample representative of a seed lot, typically 200-600 seeds, is placed on the surface of moistened blotter paper or between layers of moistened blotter paper and placed in a temperature-controlled environment, with or without light, for a period of time. Alternatively, seed samples are sown in soil, sand, or peat- or bark-based growing media and placed in a temperature-controlled environment or greenhouse. After some period of time, the resultant seedlings are evaluated, counted if considered to be normal, and the number of normal seedlings from the number of seed sown used to calculate the percent germination.

Standardization of testing conditions and proper evaluation of "normal" seedlings are necessary for germination test results to be useful. Various bodies, such as the Society of Commercial Seed Technologists and the International Seed Testing Association, publish standardized testing conditions and run certification schemes to assure necessary training for those evaluating germination test results.

Standard germination testing measures the percentage of a seed lot which will produce normal seedlings under generally optimal environmental conditions. These tests do not measure "vigor", variously defined as the ability of seed to germinate under less than optimal conditions and/or the ability of a seed to produce a seedling which grows more vigorously than others. Many tests have been developed attempting to measure and to quantify "vigor". Most involve testing germination under suboptimal conditions and/or measuring size or growth rates of seedling tissues, such as roots or cotyledons.

Embodiments of the seed analysis system disclosed herein assist in the analysis of the individual seed for purposes of determining percent germination of a seed lot.

Example Embodiments

Figure 8:
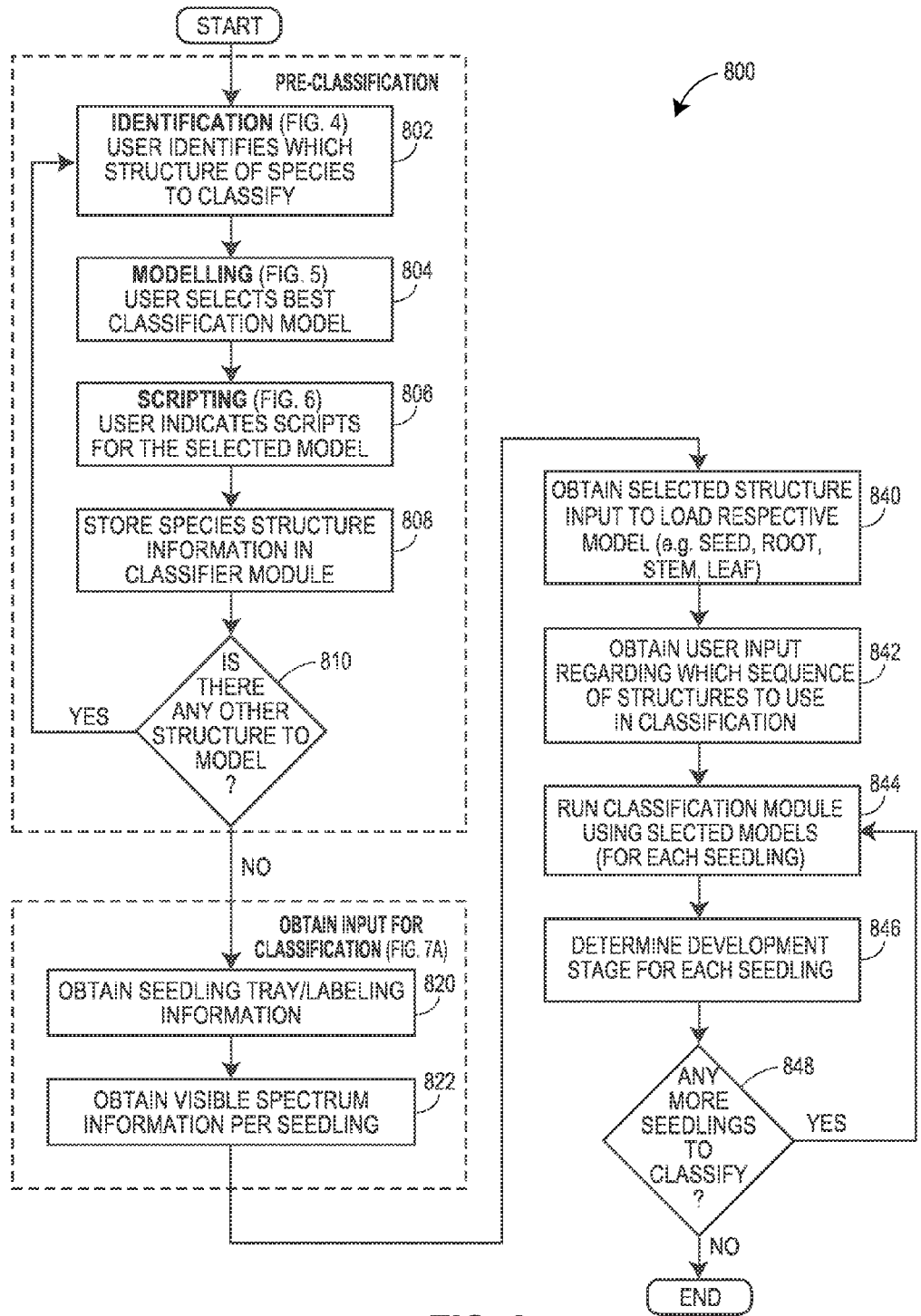
FIG. 8 is an exemplary flow diagram that provides an alternative embodiment of the method of FIG. 3. wherein the spectral analysis uses only a single spectral input along with a pre-classification procedure.

FIG. 8 illustrates an example embodiment that illustrates the combination of the pre-classification process with the seed classification process that uses a single spectral input. Blocks 802-810 are similar to blocks 202-210 of FIG. 3 and blocks 840-842 are similar to blocks 220-248. This embodiment presents an example embodiment of FIG. 3, wherein the overall classification process 800 uses only a single visible spectrum input at block 822.

Figure 9:
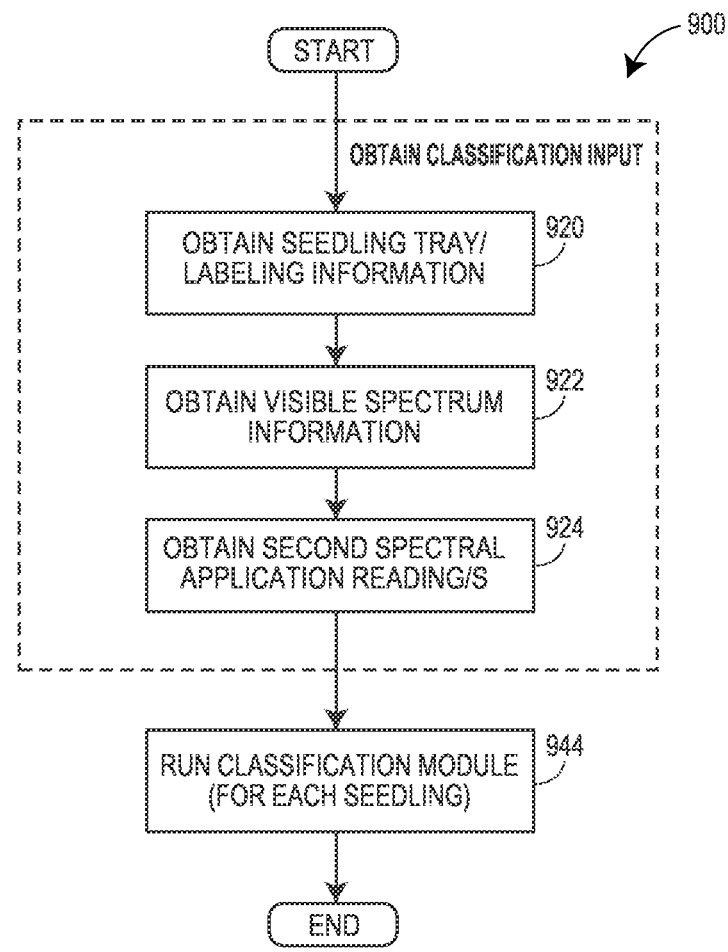
FIG. 9 is an exemplary flow diagram that provides an alternative embodiment of the method of FIG. 3. wherein the spectral analysis uses a multiple spectral input.

FIG. 9 illustrates an example embodiment of FIG. 3, wherein the pre-classification process of FIG. 3 has already been run to produce the classification scripts as described above for use at block 944. FIG. 9 also illustrates an example embodiment wherein multiple visible spectrum input is obtained (blocks 922 and 924). FIGS. 8-9 are presented to show examples of the alternative embodiments that are supported by FIG. 3 and the application specification as a whole.

Other alternative embodiments, which are not expressly disclosed herein to keep the application at a practical size, are also covered despite their express instance not being expressly described as one of ordinary skill in the art would have knowledge of the alternatives in light of this disclosure.

Other Embodiments and Examples

The above embodiments that use multiple spectral inputs may include Hyperspectral imaging, which collects and processes information from across the electromagnetic spectrum. Multi-spectral imaging collects and processes information from specific wavelengths across the electromagnetic spectrum.

Hyperspectral imaging is part of a class of techniques commonly referred to as spectral imaging or spectral analysis. Hyperspectral imaging is related to multispectral imaging. The distinction between hyperspectral and multispectral is usually defined as the number of spectral bands. Multispectral data contains from several to tens of bands. Hyperspectral data contains dozens to hundreds of bands.

Both methods of data collection and processing may be used herein to determine the classification of the seed, which may be used to determine the developmental stage of the germinating seed and thus the "germination percentage" of the lot of seeds.

FIG. 18A-18G illustrate images that may be produced with the seed analysis system and methods described herein, and then used to determine seed classification, and thus seed lot germination.

FIG. 18A illustrates a visible spectrum image that is produced using a color camera, that may or may not use a flash. Without the flash, ambient light is used to produce the captured image of the seed. FIG. 18B illustrates example of height image data that may be captured using a laser triangulation system. The leaves are seen as green and the stem is seen as red. The analysis system may produce different results based upon setting different height thresholds. The seedling structure which contains chlorophyll shows up on this image. It is a grayscale image (0-255). Minimum height is black, Maximum height is white FIG. 18C illustrates an example of a combination of high and low chlorophyll image data. It can be seen that the intensity of the chlorophyll amount of the leaf is captured as being different from the chlorophyll amount of the stem.

FIG. 18D illustrates an example of a result image after a modeling script was applied to the original image of FIG. 18A. For example, the original image of 18A was processed with a pre-classification process that removed the background data from the image except the seed structure data and the well border to generate a set of model parameters. The pre-classification process also used the height image of FIG. 18B and the low-high chlorophyll image of 18C to generate a set of model parameters. When the model parameters are applied to the images, the resultant image appears as illustrated in FIG. 18D. The set of modeling parameters may be used to form a script for use in subsequent seed analysis. FIG. 18D illustrates the result of overlapping the chlorophyll data over the original color image. As may be observed from the illustration in FIG. 18D, the seed coat and the seed root are distinguished from the stem and the leaf. This seed may then be classified as having a root.

Additionally, the seed analysis system may produce any other information that a user may require, such as any information of the dimensions of the root or other seed structure. For example, a user may request information such as total area, length, width, percentage of overall structure, cholorophyll, height etc. Additionally, spectral image sources and detection devices may be adjusted at any angle or combined to generate 3-dimensional information about the seed. Additionally, the seed may be analyzed over time. Any and all possible combinations of information that may be generated from the seed analysis system are covered herein.

With the processing and modeling parameters applied, the resultant image of FIG. 18D may be produced. For example, the image of FIGS. 18A-18C may be combined to leave only the seed coat and the seed stem and well border identified with visible black coloring, as illustrated in FIG. 18D.

Figure 18E:
Figure 18F:
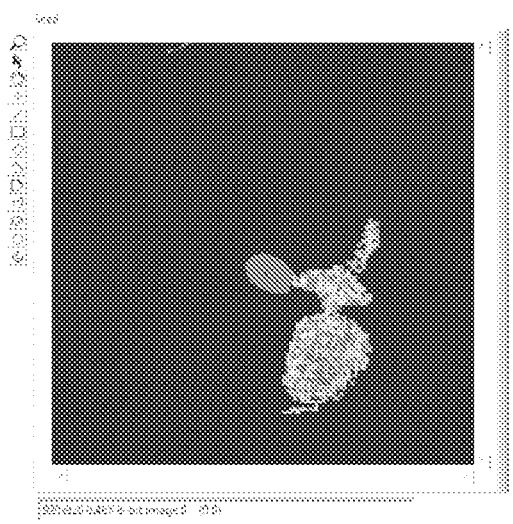

The seed analysis system may apply further operators when generating a set of model parameters that are used to distinguish seed structures. For example, if a set of parameters is applied, such as Red and Green image planes adjusted by MULTIPLY & DIVIDE operator plus other noise removal steps, then the seed analysis system may produce the image of FIG. 18E. FIG. 18E illustrates an image where the seed coat is now not visible so that only the root, stem and leaf remain visible. With further processing, the seed analysis system may produce the image of FIG. 18F. if a set of parameters is applied, such as Hue plane subtracted by Green plane plus other noise removal steps, then the seed analysis system may produce the image of FIG. 18F. FIG. 18F illustrates an image where the root is now not visible so that only the seed coat, stem and leaf remain visible. Any possible resultant image that distinguishes every possible seed structure, and substructure, and other information may be produced with the seed analysis system and methods described herein.

Figure 18G:
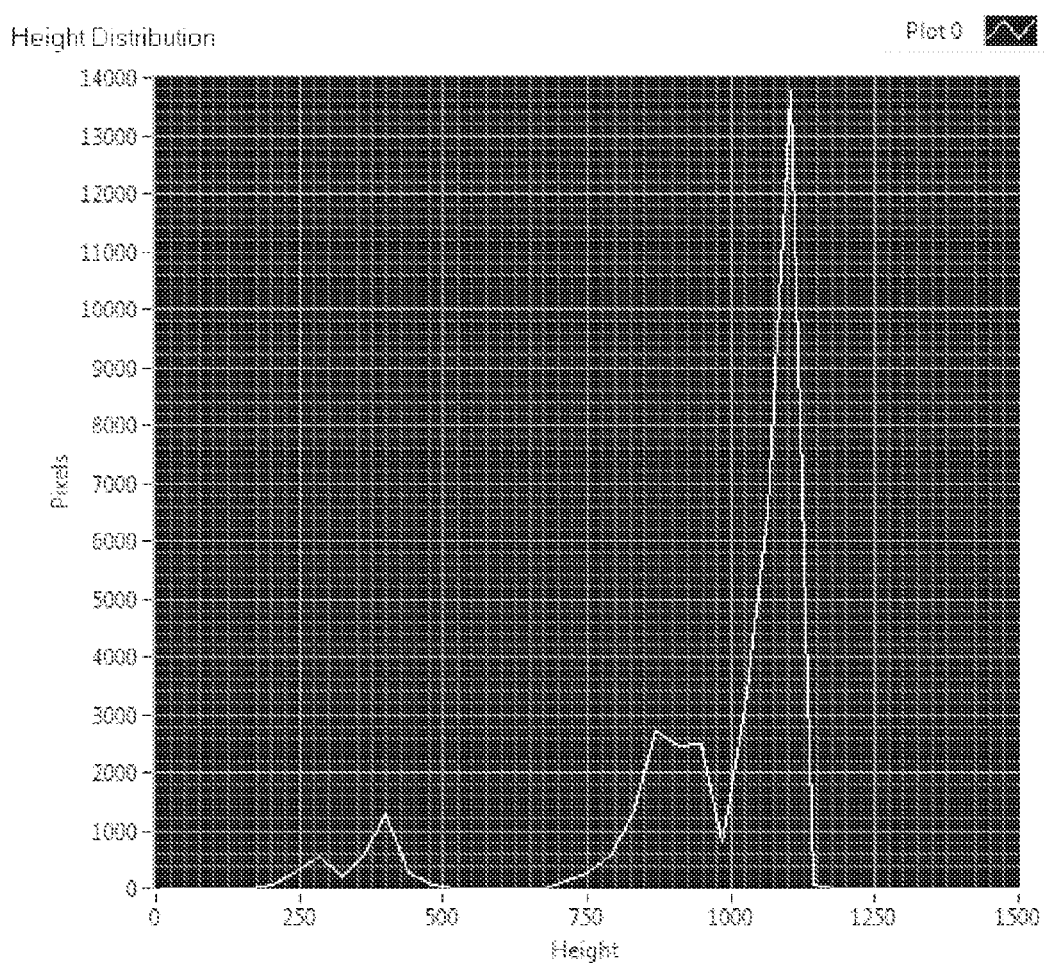

For example a graph of height versus pixels may be used to show the results of FIG. 18G. FIG. 18G illustrates three height classes. For example, a first height class appears at around 2.5-8 mm., a second height class at 7.5-8.5 mm., and a third height class at 10-12 mm. The first height class may be used to indicate a stem. The second and third height classes may be used to indicate first and second leaf structures.

The seed classification system and methods described herein may produce complex classification data or simpler classification data as is specified by the commercial seed industry. The American Seed Trade Association (ASTA) has rules that define a normal and healthy seedling. The AOSA, (Association for Official Seed Analysts) publication "2010 AOSA Rules for Testing Seeds" is incorporated by reference herein so that the seed analysis system and methods described herein are configurable to produce classification based on the AOSA seed structure descriptions. Also, the ISTA, (International Seed Testing Association) publication "International Rules for Seed Testing" Edition 2011 is incorporated by reference herein for the same reasons.

The SCST (Society of Commercial Seed Technologists) produce a training manual, "Seed Technologist Training Manual," whose definitions are incorporated herein by reference. The manual includes definitions of a normal and abnormal seedling as follows:

Normal seedling. A seedling with all essential structures present and capable of developing into a plant under favorable conditions; certain defects may be present if they are judged to be not so severe as to impede further development of the plant (see abnormal seedling).

Abnormal seedling. A seedling that does not have all the essential structures or is damaged, deformed or decayed to such an extent that normal development is prevented (see normal seedling).

The seed analysis system and methods described herein are configurable to produce a classification based on the Society of Commercial Seed Technologists seed structure descriptions.

Any general spectral detection/recording device may be used in place of camera 1. Camera 1 may be a charge coupled device (CCD) digital camera. The camera may be equipped with a filter that allows only the light produced from photosynthesis fluorescence of chlorophyll molecules to reach the CCD. Light for this process may be derived from any source which provides photosynthetically active radiation. Photosynthetically active radiation, often abbreviated PAR, designates the spectral range (wave band) of solar radiation from 400 to 700 nanometers that photosynthetic organisms are able to use in the process of photosynthesis.

Information from chlorophyll fluorescence at the pixel level may be used to produce unique 16 bit plane of information for the FOV (or image). This information is derived from the intensity of the signal reaching the CCD. In simple terms a picture is developed for the seed or seedling parts which are undergoing chlorophyll fluorescence. This may produce a hyperspectral plane of information for the field of view (seed or seedling being studied).

By using a triangulation technique in the system and methods described herein, by using a 650 nm laser line generator with a 665 nm low cutoff filter, and by scanning the laser line across the field of view of an area scan camera and recoding the intensity information as well as the positional information of the reflected light on a frame by frame basis, one may apply an algorithm that produces a 16 bit plane of information derived from the intensity of the signal which is the chlorophyll florescence, as well as the positional information which is the x, y, and z (or location and height) of those seed or seedling parts which are undergoing chlorophyll fluorescence.

Photosynthetic yield is a well established measurement of the light use efficiency of a plant. By repeating this process with the laser producing a lower or higher amount of energy, one may also determine the photosynthetic yield of the seed or seedling parts. This information may also be stored and displayed as a 16 bit plane of information derived from hyperspectral imaging.

It is well appreciated that many other hyperspectral spectra wavelengths could be used which provide specific information to help classify seeds or seedlings into morphological parts or seed structures.

For instance many roots fluoresce in the UV range and useful information such as moisture status of morphological parts useful for classification of morphological parts is easily obtainable from the NIR spectra.

It is also well appreciated that many other multispectral sources of information could be used that may offer other useful information to help classify seeds or seedlings into morphological parts. One such example would be an infrared camera which would record the heat being generated by the metabolic processes activated in the germination process.

With the seed analysis system and methods described herein, planes of information may be developed from both multispectral and hyperspectral information for the field of view (e.g., as associated by the germination container, e.g., well 2, well plate 4, tray 6) which contains seed and seedling morphological parts as well as the testing apparatus used to support growth (germination container) and source of moisture (blotter).

These planes of information contain data which may be used in combination to correctly and accurately determine the type of the plant parts present, the stage of germination, and ultimately the "percentage germination" of a lot of seed as well as information useful in determining the seedling vigor.

With this information many approaches may be used to correctly identify and measure multiple characteristics of unique morphological parts which comprise the seed or seedling using the multispectral and hyperspectral information.

Once the seedling parts have been identified a stage of germination can be determined and thus the "percentage germination" of a seed lot.

When a given seed/seedling reaches a defined stage of germination, it is classified as "germinated" and a "percent germination" figure determined for the seed lot being tested.

Further information is provided on the stage of germination. At any given time this information can be recorded and stored. For any give time size, shape, height, shape, volume, photosynthetic activity, and color information can be stored. Stored information over time may also be used to determine growth statistics for germinated seeds.

Multiple criteria can be used to define when "germination" has been reached. Criteria may be applied to each morphological seedling part to satisfy the requirements for normal and healthy.

An example of obtaining spectral input, which may be substituted or incorporated with any of the methods described herein includes using Scaled Calibrated RGB (RED-GREEN-BLUE) images of portions of the well plate, where the background is either a known colored blotter or soil. RGB images may be converted to HSL (HUE-SATURATION-LUMINESCENCE) data. HSL planes may be used for classification since plant parts and background may be more easily differentiated using this technique.

The image acquired may be a bitmap that includes a relative chlorophyll and height map of the plants. Objects that fluoresce in response to the stimulus light wavelength are collected, the stimulus light is filtered out using an optical band-pass filter. The intensity of the light and the position of the light on the ccd are recorded. The camera is positioned directly above and perpendicular to the seed sow surface. The lasers are projected parallel to the Y axis of the camera and at a slight angle in the Z axis. This allows for triangulation to produce an height and intensity pixel for every X,Y pixel in the seed sow plane. Frames are sampled as the plate is scanned in the Y direction (perpendicular to the laser line) across the sow plane. Sampling Resolution is only limited by scan speed and camera resolution. Resolutions of less than 50 um (in X,Y and Height) per pixel are achievable using such a imaging resolution.

Furthermore the laser may be modulated to produce a large dynamic range for the fluorescence intensity values. Since the geometry of the laser camera and lens are fixed geometric correction is applied to produce an accurate scaled bitmap for height and intensity data planes. Ratios of different stimulation intensity maps can be used to produce additional information about the plant part (ie Photosynthetic Yield calculations). All these planes of information will be critical to the final classification of the plant parts.

An example classification process may include the following: Classification of plant parts and plant stages may be determined using multiple planes of information as produced by the acquisition process. The information planes include: Red, Blue, Green, Hue, Saturation, Luminescence, Intensity, Pixel Z Height, Value, and Chlorophyll Fluorescence. Ratios between planes and transformations of planes may also be produced.

Classification may be a two-stage process: the first stage may be to separate the image information into regions of interest. The primary regions of interest are background (non plant part such as soil blotter or other growth media), Seed, Root, Stem and Leaf. Sub classifications of plant parts are accomplished based on morphological data (length, width area, location relative to primary plant part regions). Sub classification of plant parts include seed, split, root tips, root, hook, stem, partially open leaves and fully open leaves. The second stage of classification may be to use the plant part region of interests to determine the germination stage. The germination stages may include Seed, Seed Split, Root Tips, Root Hook Roots, Stem, Leaf Unfolding, and Fully Open Leaf or leaves. With accurate plant part classifications (as produced in stage 1 of the classifier) the germination stage determination may be performed using a set of classification rules or model parameters. These rules or parameters may be based on the morphology (size, shape) and presence of the different plant parts. Additional accuracy and efficiency of stage determination may be enhanced using historical information from previous classifications of the seed under test (results may be stored/cached in a database of the seed analysis system).

Example pre-classification and classification approach:
Background (Non Plant Part) Removal Blotter media is chosen to have a unique range of HSL or RGB signature. Pixels with is known signature are marked as background. The background signature can be optimized during classification to shift the spectral signature to better match the exact spectral signature of the current image. Runtime optimization can minimize any slight change in blotter wetness or lighting changes over time. A binary mask is produced for plant part and background region of interest. For soil samples the chlorophyll information produces binary mask since only stem and leaf (parts with chlorophyll) are present.

Separation of Chlorophyll and Non Chlorophyll Parts.

Using the intensity plane produced from the fluorescence the plant parts can be separated into 2 regions parts with chlorophyll (typically leaf and stem but can be customized for species dependant variations)

Seed Part Separation

Seed is determined using color planes. The search is limited to non-chlorophyll (or low chlorophyll) plant parts. Red-Blue Ratios is an example of color plane use for seed determination. Height data and morphological filters (seed has known size ranges and height) further enhance the seed separation Root Part Separation Roots have a strong separation from seed in the saturation plane. Roots are much whiter than other plant parts. Unfortunately it is very difficult to separate root and stem based solely on color. Using chlorophyll imaging information a clear separation between stem and root is determined.

Leaf Stem Separation

Leaf stem separation is determined using relative chlorophyll yields and morphological information. Chlorophyll yields is a good measure of separating the stem and leaf from each other. Part thickness filters also can be used to aid in determine leaf from stem. Additional information planes including height and intensity can be used to enhance the accuracy of this step. No single information plane alone has proven successful in making the leaf stem separation determination.

Sub Classification

Splits—root/leaf regions which overlap the convex hull of the seed region of interest are classified at possible seed split regions.

Root Tips—roots/stem regions within 2 radius of the seed region are marked as root tip candidates. The root tip is analyzed for size and shape to make the final determination.

Root Hairs—Outer perimeter of roots morphology.

Stage Determination

The results of plant part classification are used to determine the current germination phase.

Leaf Present

If the leaf region area morphology is consistent with leaf (area relative to seed, shape number of leaves) the stage is determined to be 'Leaf Present'.

Stem

When no leaf is present but stem is present the stage is 'Stem'. The stem region is filtered by minimum length and thickness to avoid misclassification of stem until a full stem is determined.

Root Hooks and Tip

When root region is present but no leaf or stem has emerged the stem is in one of 3 possible stages: root, hooks or tip. The difference between these three stages is purely morphological. Once the root has reached a critical length or root hairs are present the stage is marked to be 'Root'. If the root region length to thickness is low (3:1 or less) and restricted to the area near the seed region (actually overlapping or emerging from the seed coat) the stage is 'Tips'. The morphology between tips and roots is hooks. Hooks may be classified by length, chlorophyll content and or height.

Seed Split

When no stem or leaf region exists and the root is restricted to the convex hull of the seed coat the stage may be 'seed split'. If the area of the split is above a threshold (relative area to seed coat area) this classification is made.

Seed

If only seed region is present after stage 1 of classification the seed can be analyzed for size and shape to determine if the seed is present. If the morphology is consistent with the current seed species the stage is determined to be 'Seed'.

Empty Seed

When all known stages fail the classifier considers the seed under test to be not present.

Figure 22:
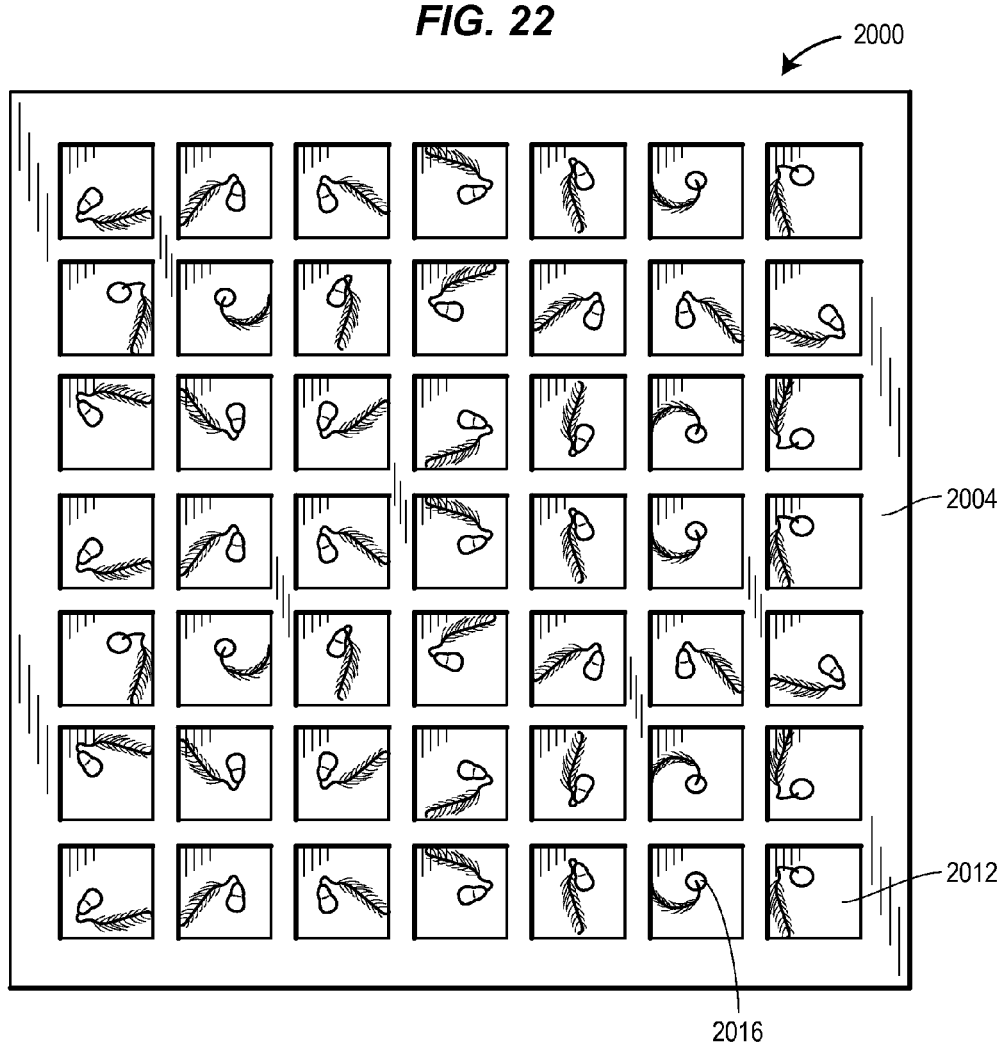
FIG. 22 is a diagram of an exemplary seed holding device configured to hold one or more seeds/seedlings for analysis.
Figure 23:
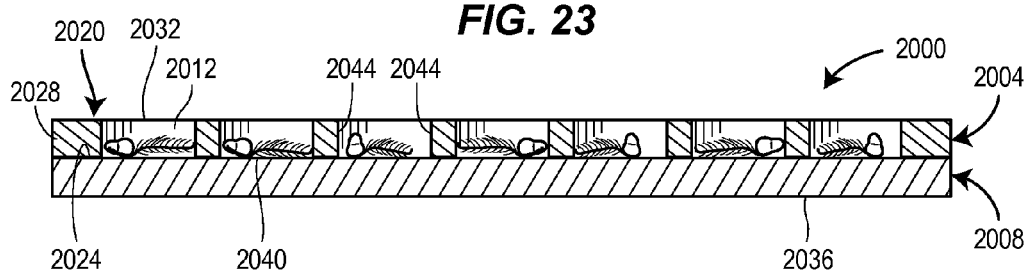
FIG. 23 is a cross-sectional view of the seed holding device of FIG. 22.

FIGS. 22 and 23 depict another example of a seed holding device 2000 that may be used with or in connection with the seed spectral analysis system 200. The seed holding device 2000 is a grid-like structure, but may be a different structure in other embodiments. The exterior dimensions (e.g., the length and/or width) of the seed holding device 2000 may be standard dimensions (e.g., pre-determined dimensions) or may be determined and vary based on, for example, the size of the platform stage 80 and/or other components of the seed spectral analysis system 200. The seed holding device 2000 generally includes a top layer 2004, a bottom layer 2008 coupled to the top layer 2004, and a plurality of wells 2012 disposed in the seed holding device 2000. The wells 2012 are configured to hold (e.g., encompass, isolate) a plurality of seeds 2016 (e.g., one or more of the seeds 1 described above) such that the seeds 2016 are encourage or induced to stay in their respective wells 2012 such that roots growing from the seeds are largely and effectively kept from crossing into any adjacent wells 2012.

Figure 24:
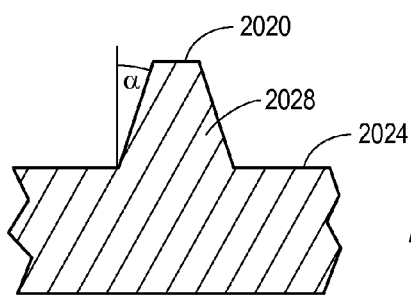
FIG. 24 is a cross-sectional view of another exemplary seed holding device configured to hold one or more seeds/seedlings for analysis.

The top layer 2004 has or defines a top surface 2020 of the seed holding device 2000 and a lower surface 2024. The top layer 2004 also has or defines a plurality of walls 2028 that extend transverse to and between the top surface 2020 and the lower surface 2024. As shown in FIG. 23, the walls 2028 can extend generally perpendicularly between the top surface 2020 and the lower surface 2024 (i.e., the walls 2028 are generally straight flat or vertical walls). In other examples, the walls 2028 can extend at other angles relative to the top or bottom surfaces 2020, 2024. As shown in FIG. 24, the walls 2028 can be oriented at an angle α relative to vertical (i.e., relative to a line perpendicular to the top surface 2020 and the lower surface 2024). The angle α can be any angle between approximately 0 and approximately 90 degrees. The angle α can, for example, be between approximately 0 and approximately 15 degrees. In one example, the angle α is approximately 8 degrees. Moreover, the walls 2028 can, in some forms, be rough and varied depending on the specific material of the top layer 2004 and the type(s) of tool(s) used to form the walls 2028. Thus, it should be appreciated that the specific representation of the walls 2028 in FIGS. 23 and 24 is schematic in nature and not intended to necessarily depict the true and accurate character of the device.

The top layer 2004 further includes openings or apertures 2032 in the seed holding device 2000. More particularly, the openings or apertures 2032 are defined by the walls 2028 in the top surface 2020 of the seed holding device 2000. The openings 2032 in FIG. 22 have a square shape (when viewed from the top, as shown in FIG. 22), but may, in other examples, have a circular, rectangular, triangular, irregular, or other suitable shape.

As shown in FIG. 23, the seeds 2016 can be seated on the bottom layer 2008. The bottom layer 2008 has or defines a bottom surface 2036 of the seed holding device 2000 and an upper surface 2040. The bottom layer 2008 can be, as noted above, coupled to the top layer 2004. More specifically, the upper surface 2040 of the bottom layer 2008 can be coupled to the lower surface 2024 of the top layer 2004. This coupling can be accomplished in any number of ways. In this example, the bottom layer 2008 can be coupled to the top layer 2004 by virtue of friction between the layers 2004, 2008, and/or any humidity/moisture present in the seed holding device 2000. In other examples, the bottom layer 2008 can be coupled to the top layer 2004 using or via an adhesive (e.g., glue, cement, paste, etc.), a fastener (e.g., a nail, pin, etc.), or some other means. The bottom surface 2036 is configured to rest on a support surface, such as the platform stage 80, for the seed holding device 2000.

The seed holding device 2000 can be made of or from one or more different reusable and/or disposable materials. The top layer 2004 can be made of or from a first material, such as a foam material (e.g., closed cell foam), a plastic material (e.g., hard plastic), silicone, blotter paper, or some other material, while the bottom layer 2008 can be made of or from a second material (e.g., blotter paper, filter paper, other issue paper, silicone, etc.) different from the first material. In the depicted example, the top layer 2004 is made from closed cell foam, while the bottom layer 2008 is made of blotter paper. In other examples, the top layer 2004 and/or the bottom layer 2008 can be made of or from one or more different and/or additional materials. For example, a top portion of the bottom layer 2008 can be made of blotter paper and a bottom portion of the bottom layer 2008 can be made of hard plastic. In further examples, the top layer 2004 and the bottom layer 2008 can be made of the same material. For example, both the top layer 2004 and the bottom layer 2008 can be made of blotter paper. It will be appreciated that any number of other materials can alternatively or additionally be used.

Although the seed holding device 2000 is described herein as including or having two separate layers, i.e., the top layer 2004 and the bottom layer 2008, the seed holding device 2000 can, in some examples, be a unitary, integrated, and homogenous structure, such that one layer provides the structure described above (e.g., side walls, wells, top surface, etc.) instead of the top layer 2004 and the bottom layer 2008. Alternatively, the seed holding device 2000 can include more than two layers. For example, the seed holding device 2000 can include a third layer (e.g., blotter paper) positioned and coupled between the top layer 2004 and the bottom layer 2008 or below or under the bottom layer 2008.

The seed holding device 2000 can include any number of wells 2012. For example, the seed holding device 2000 can include six wells 2012, twenty-four wells 2012, ninety-six wells 2012 or other any odd or even other number of wells 2012. The plurality of wells 2012 are formed or defined by the top and bottom layers 2004, 2008, particularly by the walls 2028 and the openings 2032 of the top layer 2004, and the upper surface 2040 of the bottom layer 2008. As shown in FIG. 23, the walls 2028 form or define the closure sides 2044 of the wells 2012, the upper surface 2040 forms or defines a bottom surface of each of the wells 2012, and the openings form or define a top access portion for each of the wells 2012. In the example depicted by FIG. 23, each of the wells 2012 includes a rectangular cross-sectional space configured to hold one of the seeds (FIG. 23 illustrates the rectangular cross-section of each of the wells 2012). In the example depicted by FIG. 24, each of the wells 2012 includes a trapezoidal cross-sectional space configured to hold one of the seeds. Each of the wells 2012 has a depth in a range of approximately 0.5 mm to approximately 24 mm. In one example, each of the wells 2012 has a depth of approximately 1 mm. In versions where the well depth is relatively small (e.g., less than or equal to 15 mm, less than or equal to 10 mm, less than or equal to 5 mm, less than or equal to 1 mm, etc.), the small well depth can advantageously improve the field of view of the camera 30 or camera 40 of the system described above. That is, because the camera(s) 30, 40 is/are located toward the middle of the seed holding device 2000, the side walls 2028 of the wells 2012 located toward the periphery of the field of view tend to obstruct part of the well 2012. Thus, it should be appreciated that deeper side walls 2028 obstruct more of the well 2012. Hence, in some applications, shallower wells 2012 can advantageously provide a more accurate image of the contents of each well 2012 on the support device 2000. Further yet, by orienting the side walls 2028 at an angle α relative to the vertical, blind spots may be eliminated or at least reduced, thus further improving the field of view of the camera 30 or camera 40 of the system described above.

In other examples, the plurality of wells 2012 can be formed or defined with different sized and/or shaped components. Accordingly, the plurality of wells 2012 can, in other examples, provide a different sized and/or shaped space (e.g., a cylindrical space) configured to hold one of the seeds therein. Additionally or alternatively, the plurality of wells 2012 can have a different depth (e.g., a depth in a range of between 0 and approximately 0.5 mm or a depth upwards of 24 mm).

Advantageously, the seed holding device 2000, particularly the components of the seed holding device 2000, can be customized based on the plurality of seeds 2016 to be held therein. The top layer 2004, the bottom layer 2008, and/or the wells 2012 can, for example, be customized. The customization can be based, at least in part, on one or more characteristics, such as for example, the name, type, size, structure, root size and/or shape, volume, photosynthetic activity, color information, other information, or combinations thereof, of the seeds 2016. The shape, material, length, width, depth, diameter, other dimensions, or combinations thereof, of the top layer 2004, the bottom layer 2008, and/or the wells 2012 can be customized based on the seeds 2016. For example, when the seeds 2016 have larger roots, a thicker bottom layer 2008 and deeper wells 2012 may be utilized to ensure that the roots do not grow into adjacent wells 2012. Alternatively or additionally, the number of the wells 2012 disposed in the seed holding device 2000 can be customized. For example, when there are twenty-four seeds 2016 to be held in the seed holding device 2000, the seed holding device 2000 can be customized to include twenty-four wells 2012. As a result of the described customizability, the seed holding device 2000 can be specifically and optimally configured to hold the seeds 2016, allow the seeds 2016 to grow therein, and allow the seed spectral analysis system 200 to optimally obtain image data for one or more of the seeds 2016 and classify the one or more seeds based on the obtained image data.

Figure 25:
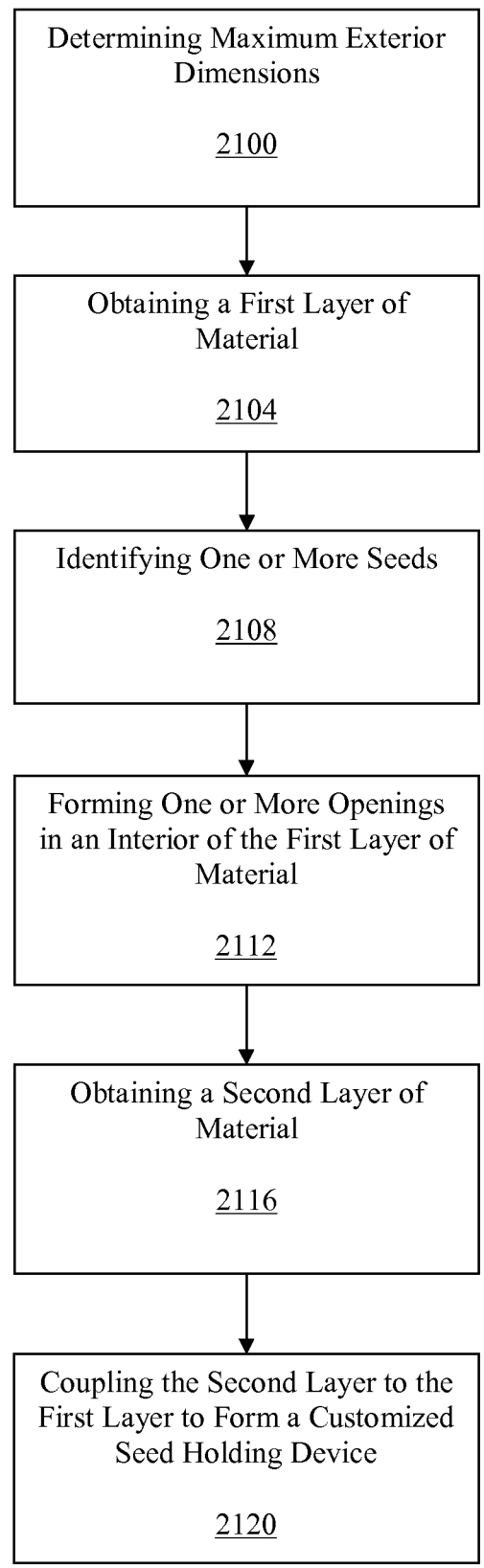
FIG. 25 is a process flow chart showing one version of a method for providing a customized seed holding device in accordance with the present disclosure.

FIG. 25 depicts an exemplary method or process of providing a customized seed holding device (e.g., the seed holding device 2000). The method or process may be performed or implemented using or with the seed spectral analysis system 200, particularly the customization module 121 included therein, and/or with some other system or device (e.g., a personal computing device) or entirely manually.

The method or process first includes determining maximum exterior dimensions of the seed holding device (block 2100). Determining the maximum exterior dimensions may include determining a length, a width, a depth, other dimension, or combinations thereof, of seed holding device. This may include, for example, determining the exterior dimensions of one or more layers of the seed holding device (e.g., the top layer 2004, the bottom layer 2008, some other layer, etc.). The maximum exterior dimensions may be determined based on one or more sets of standard dimensions or based on dimensions of other components of the seed classification system. For example, the maximum exterior dimensions may be determined based on the dimensions of a platform stage, such as the platform stage 80, on which the seed holding device may be located during the seed analysis. Further, the maximum exterior dimensions may be determined based on the size of a container in which the seed holding device resides during the processing.

The method or process then includes obtaining a first layer of material for the seed holding device based on the determined maximum exterior dimensions (block 2104). The first layer is generally the top layer (e.g., the top layer 2004) of the seed holding device, but need not be. The first layer of material may be a layer of foam (e.g., closed cell foam), plastic (e.g., hard plastic), paper (e.g., blotter paper), or some other material. In some examples, the first layer can be obtained by cutting the layer of material from a stock of material (e.g., a roll or magazine of material). When, for example, the first layer of material is to be a layer of blotter paper, the first layer may be obtained by cutting the layer from a cardboard roll of blotter paper.

The method or process then includes identifying or determining one or more seeds (e.g., one or more seeds 2016) to be classified by the seed classification system (block 2108). More specifically, one or more characteristics of the one or more seeds to be classified are identified or determined. For example, the name, type, size, structure, root size and/or shape, volume, photosynthetic activity, color information, other information, or combinations thereof, of the one or more seeds are identified or determined. Based on this information, it can be determined how large and deep each well for each seed needs to be. Based on this, it can be determined how may seeds can be supported on a single seed holding device having the maximum external dimensions previously determined. From this, it can be deduced how many wells can be provided on a device having those external dimensions.

The method or process further includes forming one or more openings (e.g., the one or more openings 2032) for the one or more seeds in an interior of the first layer based on the identifying (block 2112). The one or more openings may, for example, be formed or disposed in the top layer (e.g., the top layer 2004) of the seed holding device. In some examples, this may be accomplished by cutting the one or more openings directly into the interior of the first layer of material.

In some embodiments, as suggested above, the method or process further includes determining, based on the identified one or more seeds, (i) a size and/or a shape of each of the one or more openings to be formed, and/or (ii) a number of openings to be formed. In turn, forming the one or more openings may include forming the one or more openings based on the determined size and/or shape of each opening and/or the determined number of openings.

In some embodiments, the method or process further includes obtaining a second layer of material for the seed holding device (block 2016). The second layer is generally the bottom layer (e.g., the bottom layer 2008) of the seed holding device, but need not be (e.g., it may be an interior layer). The second layer of material may be a layer of paper (e.g., blotter paper, tissue paper, filter paper), silicone (it may thus be reusable), or some other material. The second layer of material can be obtained in the same manner as the first layer of material is obtained (e.g., by cutting the second layer from a stock of material) or in a different manner (e.g., the obtained second layer may be a standard-sized layer).

In the embodiments in which the second layer of material is obtained, the second layer of material can be coupled to the first layer of material (block 2020). In some embodiments, the first layer of material and the second layer of material are coupled to one another via friction and/or via the moisture present in one or both of the layers of material. For example, the moisture present in one or both of the layers of material can serve to couple and seal the two layers together. In other embodiments, the first layer of material and the second layer of material can be coupled to one another in a different manner, such as, for example, using or via an adhesive (e.g., glue), a fastener (e.g., a nail, pin, a clip), or some other way.

When the first layer of material and the second layer of material are coupled to one another, the customized seed holding device is formed. As such, the customized seed holding device includes a plurality of wells (e.g., the plurality of wells 2012) configured to hold one or more of the seeds. The plurality of wells correspond to the plurality of openings formed in the interior of the first layer of material. In one embodiment, the plurality of wells are formed by the plurality of openings, an upper surface (e.g., the upper surface 2040) of the second layer of material, and a plurality of walls (e.g., the plurality of walls 2028) that extend transverse to and between the first and second layers of material.

In turn, the one or more seeds can be placed in the one or more wells of the customized seed holding device, image data for the one or more seeds placed in the one or more wells can be obtained, and the one or more seeds can be classified based on the obtained image data, as described above.

Based on the foregoing description, it should be appreciated that the systems, devices, and methods described herein provide for a seed holding device that may be customized based on one or more seeds to be held therein and that may include a plurality of wells, which, by having a depth in the range of approximately 0.5 mm to 24 mm, have a depth that may more shallow than conventional well plates (which typically have a depth in the range of approximately 20 mm to 24 mm). The seed holding device may thus be specifically tailored to hold seeds. By utilizing these features, the disclosed systems, devices, and methods are more flexible than systems, devices, and methods that utilize conventional well plates, and may more effectively image, analyze, and classify seeds. Specifically, by utilizing shallower, customized wells to hold seeds instead of conventional well plates, an enhanced field of vision may be provided for the seed spectral analysis system.

The invention claimed is:

1. A system for classifying germinated seeds, comprising:
a seed holding device for holding the germinated seeds, the seed holding device comprising a top surface and a plurality of wells disposed in the top surface and configured to hold a plurality of seeds, each well being defined by at least one wall extending transverse to the top surface and having a bottom surface made of paper for serving as a source of moisture for the germinated seeds, the paper being customizable to accommodate the specific germinated seeds to be held; and a seed spectral analysis system configured to obtain image data for one or more of the seeds held in one or more of the wells of the seed holding device and configured to classify the one or more seeds based on the obtained image data, wherein the seed holding device comprises a top layer and a bottom layer, the top layer defining the top surface of the seed holding device and having a plurality of openings, the bottom layer having an upper surface defining the bottom surface of the wells upon which the plurality of seeds are to be disposed, each opening in the top layer defined by the at least one wall of each well.

2. The seed classification system of claim 1, wherein the wells are customized based on the plurality of seeds.

3. The seed classification system of claim 1, wherein a size or a shape of the wells is customized.

4. The seed classification system of claim 1, wherein a number of the plurality of wells is customized.

5. The seed classification system of claim 1, wherein the seed holding device is a grid-like structure.

6. The seed classification system of claim 1, wherein each well of the seed holding device has a depth in a range of approximately .5 mm to approximately 24 mm.

7. The seed classification system of claim 6, wherein each well of the seed holding device has a depth of approximately 1 mm.

8. The seed classification system of claim 1, wherein the bottom layer is formed at least partly of blotter paper.

9. The seed classification system of claim 1, wherein the seed spectral analysis system comprises:
    a scanner device configured to subject the one or more seeds to a first spectral signal;
    a recording device configured to capture a first reflection from the first spectral signal and produce the image data; and
    a classification module configured to classify the one or more seeds based on the image data.

10. A method for analyzing germinated seeds, the method comprising:
    identifying one or more germinated seeds to be classified;
    customizing a seed holding device based on the identified one or more germinated seeds, the seed holding device having one or more wells with bottom surfaces made of paper configured to hold the one or more germinated seeds, the paper serving as a source of moisture for the germinated seeds, wherein the seed holding device comprises a top layer and a bottom layer, the top layer defining the top surface of the seed holding device and having a plurality of openings, the bottom layer having an upper surface defining the bottom surface of the wells upon which the plurality of germinated seeds are to be disposed, each opening in the top layer defined by the at least one wall of each well;
    placing the one or more germinated seeds in the one or more customized wells;
    obtaining, via a processor, image data for the one or more germinated seeds placed in the one or more customized wells; and
    classifying, via the processor, the one or more germinated seeds based on the obtained image data.

* * * * *